United States Patent [19]
Bagi et al.

[11] Patent Number: 6,017,885
[45] Date of Patent: Jan. 25, 2000

[54] IGF/IGFBP COMPLEX FOR PROMOTING BONE FORMATION AND FOR REGULATING BONE REMODELING

[75] Inventors: Cedo Martin Bagi, Sunnyvale; Robert Brommage, Santa Clara; David M. Rosen, San Jose; Steven W. Adams, Sunnyvale, all of Calif.

[73] Assignee: Celtrix Pharmaceuticals, Inc., San Jose, Calif.

[21] Appl. No.: 09/080,120

[22] Filed: May 14, 1998

Related U.S. Application Data

[63] Continuation of application No. 08/806,918, Feb. 26, 1997, abandoned, which is a continuation of application No. 08/450,258, May 25, 1995, abandoned, which is a continuation of application No. 08/278,456, Jul. 20, 1994, abandoned.

[51] Int. Cl.[7] .................................................. A61K 38/30
[52] U.S. Cl. .................................... 514/12; 514/3; 514/4; 514/21; 530/399; 530/303; 530/324
[58] Field of Search ......................... 514/12, 21, 3, 514/4; 530/399, 303, 324

[56] References Cited

U.S. PATENT DOCUMENTS

| | | | |
|---|---|---|---|
| 5,118,667 | 6/1992 | Adams et al. | 514/12 |
| 5,187,151 | 2/1993 | Clark et al. | 514/12 |
| 5,200,509 | 4/1993 | Spencer et al. | 530/350 |
| 5,614,496 | 3/1997 | Dunstan et al. | 514/12 |

FOREIGN PATENT DOCUMENTS

| | | |
|---|---|---|
| 0 375 438 A2 | 6/1990 | European Pat. Off. . |
| 0 375 438 A3 | 6/1990 | European Pat. Off. . |
| 0 436 469 B1 | 7/1991 | European Pat. Off. . |
| 0436469 A1 | 7/1991 | European Pat. Off. . |
| WO 88/07863 | 10/1988 | WIPO . |
| WO 89/08667 | 9/1989 | WIPO . |
| WO 90/06950 | 6/1990 | WIPO . |
| WO 92/13556 | 8/1992 | WIPO . |
| WO 92/18154 | 10/1992 | WIPO . |
| WO 94/04030 | 3/1994 | WIPO . |

OTHER PUBLICATIONS

Blum et al., "Plasma IGFBP–3 levels as clinical indicators" *Modern Concepts of Insulin–Like Growth Factors* (1991) E.M. Spencer, ed., Elsevier, New York, pp. 381–393.

Wood et al., "Cloning and expression of the growth hormone–dependent insulin–like growth factor–binding protein" *Mol. Endocrin.* (1988) 2:1176–1185.

Spratt et al., "Cloning and expression of human insulin–like growth factor binding protein 3" *Growth Factors* (1990) 3:63–72.

Martin et al., "Insulin–like growth factor–binding protein from human plasma. Purification and characterization" *J. Biol. Chem.* (1986) 261:8754–8760.

Sommer et al., "Molecular genetics and actions of recombinant insulin–like growth factor binding protein–3" *Modern Concepts of Insulin–Like Growth Factors* (1991) E.M. Spencer, ed., Elsevier, New York, pp. 715–728.

Shimasaki et al., "Identification and molecular characterization of insulin–like growth factor binding proteins (IGFBP–1, –2, –3, –4, –5 and –6)" *Prog. Growth Factor Res.* (1991) 3:243–266.

Spencer et al. "In vivo actions of insulin–like growth factor–I (IGF–I) on bone formation and resorption in rats" *Bone* (1991) 12:21–26.

Tobias et al., "Opposite effects of insulin–like growth factor–I on the formation of trabecular and cortical bone in adult female rats" *Endocrinology* (1992) 131:2387–2392.

Frost, "The pathomechanics of osteoporoses" *Clin. Orthop. Rel. Res.* (1985) 200:198–225.

Parfitt, "Age–related structural changes in trabecular and cortical bone: Cellular mechanisms and biomechanical consequences" *Calcif. Tissue Int.* (1984) 36:S123–S128.

Brewer et al., "Cloning, characterization, and expression of a human insulin–like growth factor binding protein" *Biochem. Biophys. Res. Comm.* (1988) 152:1289–1297.

Binkert et al., "Cloning, sequence analysis and expression of a cDNA encoding a novel insulin–like growth factor binding protein (IGFBP–2)" *EMBO J.* (1989) 8:2497–2502.

Shimasaki et al., "Molecular cloning of the cDNAs encoding a novel insulin–like growth factor–binding protein from rat and human" *Mol. Endocrinol.* (1990) 4:1451–1458.

Shimasaki et al., "Isolation and molecular cloning of insulin– like growth factor–binding protein–6" *Mol. Endocrinol.* (1991) 5:938–948.

Shimasaki et al., "Identification of five different insulin–like growth factor binding proteins (IGFBPs) from adult rat serum and molecular cloning of a novel IGFBP–5 in rat and human" *J. Biol. Chem.* (1991) 266:10646–10653.

Frost, *Bone Histomorphometry: Techniques and Interpretation*, R.R. Recker, ed., (1983) Boca Raton, FL. Chapter 4, pp. 37–52.

Wronski et al., "Skeletal alterations in ovariectomized rats" *Calcif. Tissue Int.* (1985) 37:324–328.

Kimmel et al., "Nondestructive measurement of bone mineral in femurs from ovariectomized rats" *Calcif. Tissue Int.* (1990) 46:101–110.

Durbridge et al., "Progressive cancellous bone loss in rats after adrenalectomy and oophorectomy" *Calcif. Tissue Int.* (1990) 47:383–387.

Miller et al., "Calcium absorption and osseous organ–, tissue–, and envelope–specific changes following ovariectomy in rats" *Bone* (1991) 12:439–446.

(List continued on next page.)

*Primary Examiner*—F. T. Moezie
*Attorney, Agent, or Firm*—Morrison & Foerster LLP

[57] ABSTRACT

IGF and IGFBP are administered to stimulate new bone formation in subjects with bone loss due to bone marrow disorders, connective tissue disorders, drugs, pregnancy, lactation, chronic hypophosphatemia, hyperphosphatasia, insulin-dependent diabetes mellitus, anorexia nervosa, cadmium poisoning, juvenile osteoporosis, Paget's disease of bone, osteoarthritis and periodontal disease. IGF-I and IGFBP-3 are optionally combined with agents that inhibit bone resorption.

8 Claims, 21 Drawing Sheets

OTHER PUBLICATIONS

Wronski et al., "Temporal relationship between bone loss and increased bone turnover in ovariectomized rats" *Calcif. Tissue Int.* (1985) 43:179–183.

Turner et al., "The effects of ovariectomy and 17J–estradiol on cortical bone histomorphometry in growing rats" *J. Bone & Mineral Res.* (1987) 2:115–122.

Wronski et al., "Estrogen treatment prevents osteopenia and depresses bone turnover in ovariectomized rats" *Endocrinology* (1988) 123:681–686.

Wronski et al., "Endocrine and pharmacological suppressors of bone turnover protect against osteopenia in ovariectomized rats" *Endocrinology* (1989) 125:810–816.

Pfeilshifter et al., "Modulation of type J transforming growth factor activity in bone cultures by osteotropic hormones" *Proc. Natl. Acad. Sci. U.S.A.* (1987) 84:2024–2028.

Bagi, C.M. et al., "Benefit of Systemically Administered rhIGF–I and rhIGF–I/IGFBP–3 on Cancellous Bone in Ovariectomized Rats" *J. Bone Mineral Res.* 9(8):1301–1312 (1994).

Bagi, C.M. et al., "The rhIGF–I/IGFBP–3 Complex Stimulates Bone Formation on Cortical and Trabecular Surfaces in the Femoral Neck of Ovariectomized Rats" *Bone and Mineral* 25(1):S5 Abstract No. 12 (1994).

Turner et al., "Tamoxifen inhibits osteoclast–mediated resorption of trabecular bone in ovarian hormone–deficient rats" *Endocrinology* (1988) 122:1146–1150.

Fisher et al., "Inhibition of osteoclastic bone resorption in vivo by echistatin, an 'arginyl–glycyl–aspartyl' (RGD)–containing protein" *Endocrinology* (1993) 132:1411–1413.

Zaidi et al., "Inhibitors of bone resorption and implications for therapy" *Curr. Opin. Therapeutic Patents* (1992) 10:1517–1538.

Gunness–Hey, "Increased trabecular bone mass in rats treated with human synthetic parathyroid hormone" *Metab. Bone Dis. & Rel. Res.* (1984) 5:177–181.

Jamall et al., "A simple method to determine nanogram levels of 4–hydroxyproline in biological tissues" *Analyt. Biochem.* (1981) 112:70–75.

Miller et al., "Changes in bone mineral and bone formation rates during pregnancy and lactation in rats" *Bone* (1986) 7:283–287.

Miller et al., "Long–term osteopenic changes in cancellous bone structure in ovariectomized rats" *Anat. Record* (1993) 236:433–441.

Bagi et al., "Comparison of osteopenic changes in cancellous bone induced by ovariectomy and/or immobilization in adult rats" *Anat. Record* (1994) 239:243–254.

Parfitt et al., "Bone histomorphometry: Standardization of nomenclature, symbols, and units" *J. Bone & Mineral Res.* (1987) 2:595–610.

Studier et al., "Use of bacteriophage T7 RNA polymerase to direct selective high–level expression of cloned genes" *J. Mol. Biol.* (1986) 189:113–130.

Squires et al., "Production and characterization of human basic fibroblast growth factor from *Escherichia coli*" *J. Biol. Chem.* (1988) 263:16297–16302.

Meacock et al., "Partitioning of bacterial plasmids during cell division: a cis–acting locus that accomplishes stable plasmid inheritance" *Cell* (1980) 20:529–542.

Daughaday et al., *Endocrine Reviews*, vol. 10, No. 1, 68–91, 1989.

Rosen et al., *Minireview*, IGF's and Osteoporosis, 83–96, P.S.E.B.M., vol. 206, 1994.

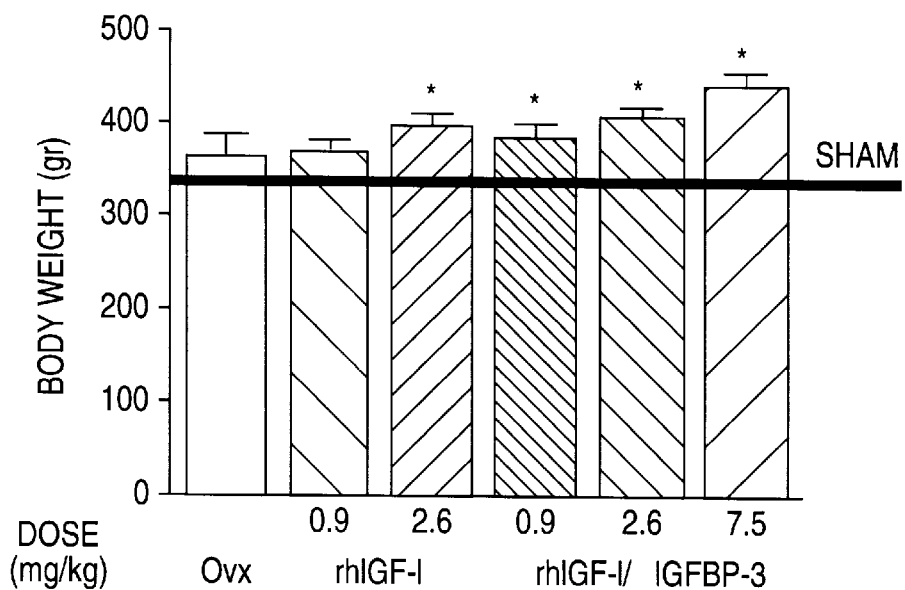
FIG. 2A  *SIGNIFICANTLY DIFFERENT FROM Ovx GROUP
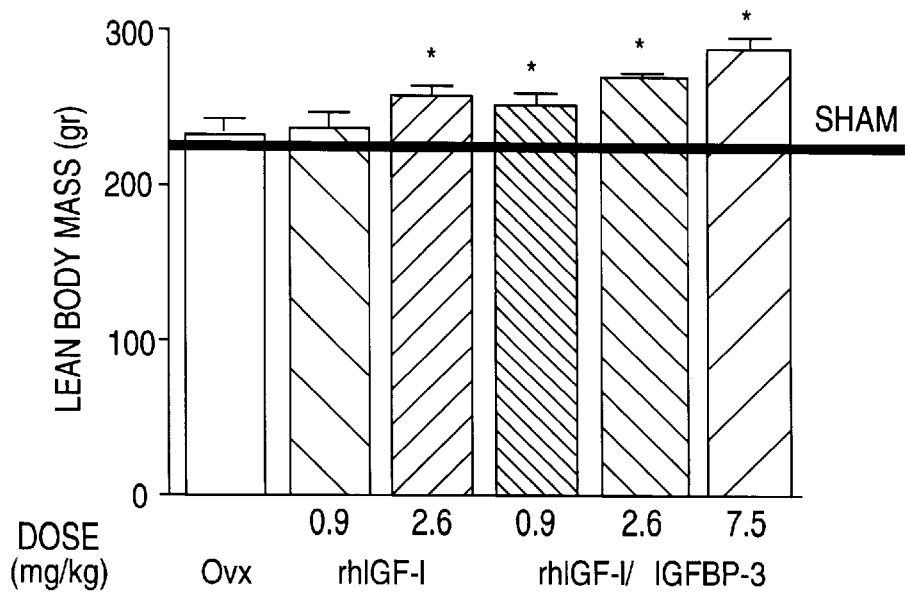
FIG. 2B  *SIGNIFICANTLY DIFFERENT FROM Ovx GROUP

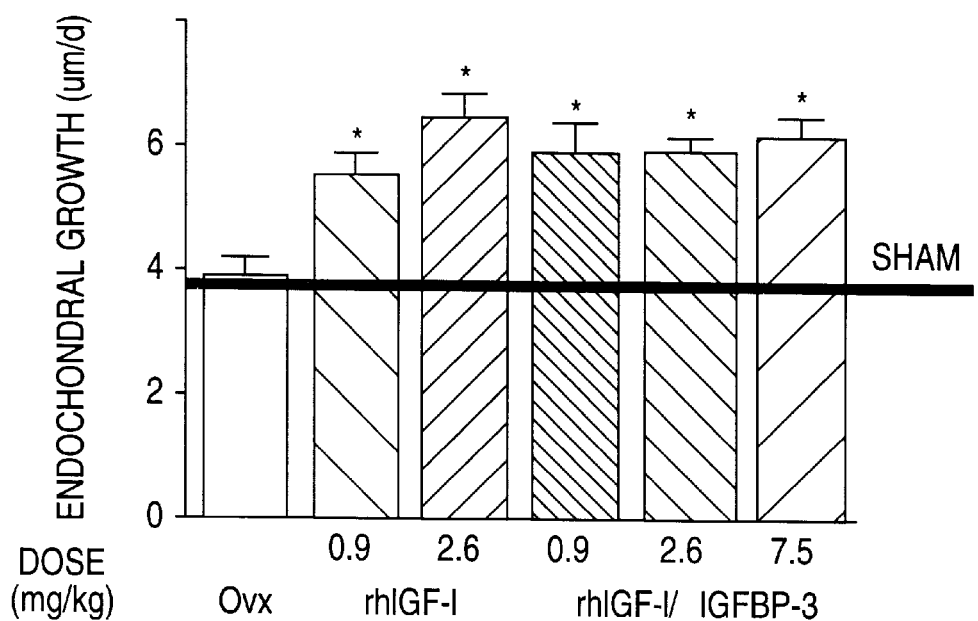
FIG. 3   *SIGNIFICANTLY DIFFERENT FROM Ovx GROUP

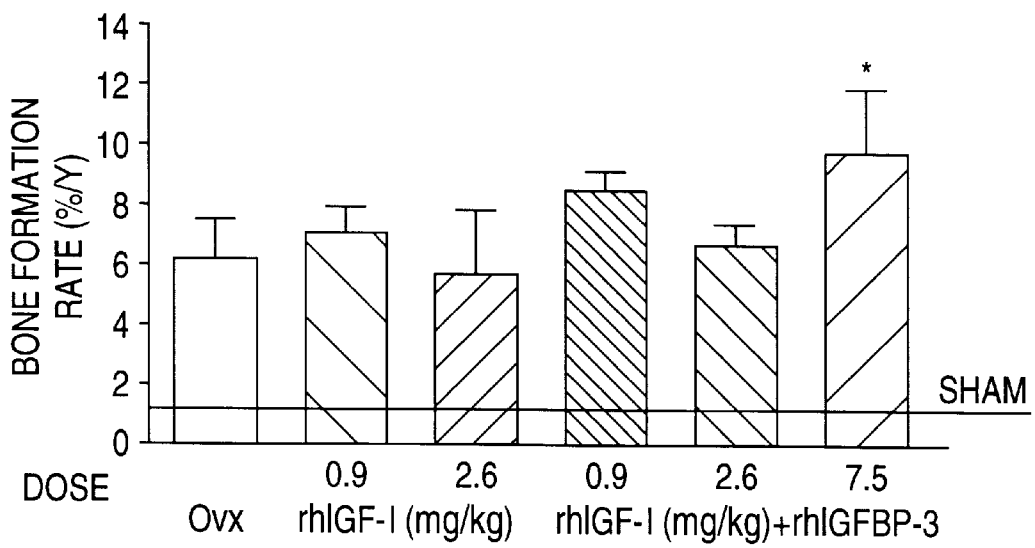
FIG. 7C  *SIGNIFICANTLY DIFFERENT FROM Ovx GROUP
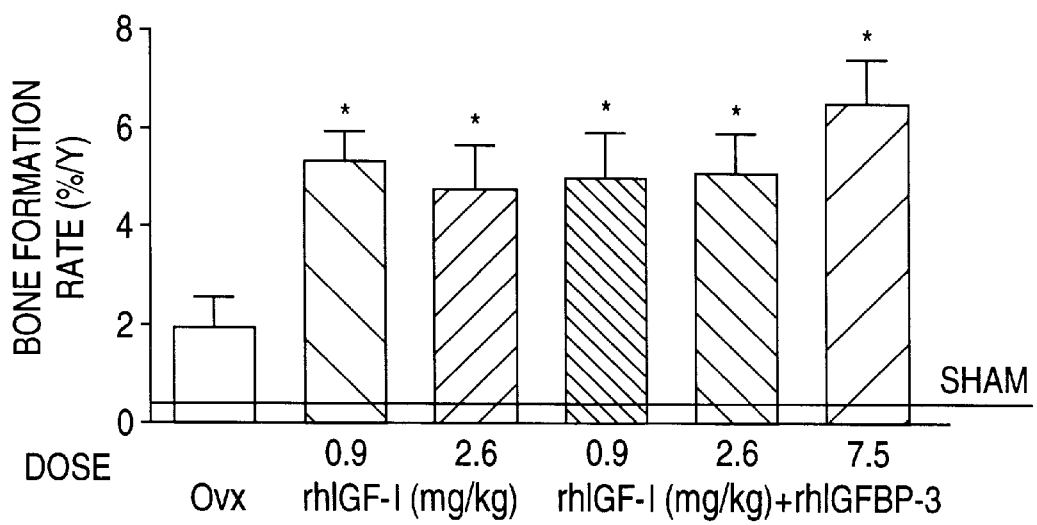
FIG. 7D  *SIGNIFICANTLY DIFFERENT FROM Ovx GROUP

GPETLCGAELVDALQFVCGDRGFYFNK
PTGYGSSSRRAPQTGIVDECCFRSCDL
RRLEMYCAPLKPAKSA

FIG. 11

```
            *
GASSAGLGPVVRCEPCDARALAQCAPPPAVCAELVRE
PGCGCCLTCALSEGQPCGIYTERCGSGLRCQPSPDEA
RPLQALLDGRGLCVNASAVSRLRAYLLPAPPAPGNAS
ESEEDRSAGSVESPSVSSTHRVSDPKFHPLHSKIII
KKGHAKDSQRYKVDYESQSTDTQNFSSESKRETEYGP
CRREMEDTLNHLKFLNVLSPRGVHIPNCDKKGFYKKK
QCRPSKGRKRGFCWCVDKYGQPLPGYTTKGKEDVHCY
SMQSK
```

\* There is a natural heterogeneity at position 5; glycine can also occur at this position.

FIG. 12

```
156  ATG GGT GCA TCT TCT GCA GGT TTA GGT CCA GTT GTT CGT TGT GAA CCA
     Met Gly Ala Ser Ser Ala Gly Leu Gly Pro Val Val Arg Cys Glu Pro
      1               5               10              15

204  TGT GAT GCT CGT GCT CTT GCT CAA TGT GCT CCA CCA GCT GTT TGT
     Cys Asp Ala Arg Ala Leu Ala Gln Cys Ala Pro Pro Ala Val Cys
                     20              25              30

252  GCT GAA CTT GTT CGT GAA CCG GGT TGT TGT TGT CTG ACT TGC GCA
     Ala Glu Leu Val Arg Glu Pro Gly Cys Cys Cys Leu Thr Cys Ala
                 35              40              45

300  CTT TCT GAA GGT CAA CCA TGT GGT ATT TAT ACT GAA CGT TGT GGT TCT
     Leu Ser Glu Gly Gln Pro Cys Gly Ile Tyr Thr Glu Arg Cys Gly Ser
                 50              55              60

348  GGT CTG CGT TGT CAA CCA TCT CCA GAT GAA GCT CGT CCT CTG CAG GCT
     Gly Leu Arg Cys Gln Pro Ser Pro Asp Glu Ala Arg Pro Leu Gln Ala
     65              70              75              80
```

FIG. 13A

```
396  CTG CTG GAC GGT CGT GGT CTG TGC GTT AAC GCT TCC GCT GTT TCC CGT
     Leu Leu Asp Gly Arg Gly Leu Cys Val Asn Ala Ser Ala Val Ser Arg
              85                  90                  95

444  CTG CGC GCC TAC CTG CTG CCA GCG CCG CCA GCT CCA GGA AAT GCT AGT
     Leu Arg Ala Tyr Leu Leu Pro Ala Pro Pro Ala Pro Gly Asn Ala Ser
              100                 105                 110

492  GAG TCG GAG GAA GAC CGC AGC GCC GGC AGT GTG GAG AGC CCG TCC GTC
     Glu Ser Glu Glu Asp Arg Ser Ala Gly Ser Val Glu Ser Pro Ser Val
              115                 120                 125

540  TCC AGC ACG CAC CGG GTG TCT GAT CCC AAG TTC CAC CCC CTC CAT TCA
     Ser Ser Thr His Arg Val Ser Asp Pro Lys Phe His Pro Leu His Ser
              130                 135                 140

588  AAG ATA ATC ATC ATC AAG AAA GGG CAT GCT AAA GAC AGC CAG CGC TAC
     Lys Ile Ile Ile Ile Lys Lys Gly His Ala Lys Asp Ser Gln Arg Tyr
              145                 150                 155                 160
```

FIG. 13B

```
636  AAA GTT GAC TAC GAG TCT CAG AGC ACA GAT ACC CAG AAC TTC TCC TCC
     Lys Val Asp Tyr Glu Ser Gln Ser Thr Asp Thr Gln Asn Phe Ser Ser
              165                 170                 175

684  GAG TCC AAG CGG GAG ACA GAA TAT GGT CCC TGC CGT AGA GAA ATG GAA
     Glu Ser Lys Arg Glu Thr Glu Tyr Gly Pro Cys Arg Arg Glu Met Glu
              180                 185                 190

732  GAC ACA CTG AAT CAC CTG AAG TTC CTC AAT GTG CTG AGT CCC AGG GGT
     Asp Thr Leu Asn His Leu Lys Phe Leu Asn Val Leu Ser Pro Arg Gly
              195                 200                 205

780  GTA CAC ATT CCC AAC TGT GAC AAG AAG GGA TTT TAT AAG AAA AAG CAG
     Val His Ile Pro Asn Cys Asp Lys Lys Gly Phe Tyr Lys Lys Lys Gln
              210                 215                 220

828  TGT CGC CCT TCC AAA GGC AGG AAG CGG GGC TTC TGC TGG TGT GTG GAT
     Cys Arg Pro Ser Lys Gly Arg Lys Arg Gly Phe Cys Trp Cys Val Asp
              225                 230                 235         240
```

FIG. 13C

876  AAG TAT GGG CAG CCT CTG CCA GGC TAC ACC ACC AAG GGG AAG GAG GAC
     Lys Tyr Gly Gln Pro Leu Pro Gly Tyr Thr Thr Lys Gly Lys Glu Asp
                 245                 250                 255

924  GTG CAC TGC TAC AGC ATG CAG AGC AAG TAG
     Val His Cys Tyr Ser Met Gln Ser Lys
             260                 265

```
      10          20          30          40          50          60
123 456 789 012 345 678 901 234 567 890 123 456 789 012 345 678 901 234 567 890
GGT GCT TCT TCT GCT GGT CTT GGA CCA GTT GTT CGT TGT GAA CCA TGT GAT GCA CGA GCT   60
TTA GCT CAA TGT GCT CCA CCA CCA GCT GTT TGT GCT GAA TTA GTT CGA GAA CCA GGT TGT  120
GGT TGT TGT TTA ACT TGT GCT TTA TCT GAA GGT CAA CCA GAT GAA GCT GTT GGT ATT TAT ACT GAA CGT  180
TGC GGT AGT GGT TTG CGT TGT TGT CGT CTG TGT CAA CCA AGC CCA TCC GCT GTT TCT CGA TTA CAA GCA TTA  240
TTA GAT GGT CGA GGT CCA GCA CCG GGT AAC GCC TCC GAA GAG GAT CGT GCG GGT  300
TTA CCT GCC CCA CCG GTG AGT TCT ACC CAT CGA GTT CAC GCA AAG GAT CCG AAA TTT CAT CCG  360
TCC GTT GAA TCT CCA AAA ATC ATT ATT AAA AAG CAC GCA AAT TTT AGT GAA AGT AAA CGT GAA  420
TTG CAC TCT AAA ATC ATT ATT AAA AAG GAT CAC GCA AAT TTT AGT GAA AGT AAA CGT GAA  480
GTG GAT TAT GAA AGC CAA TCT ACC GAC ACT CAA ATG GAG GAT ACC TTA AAC CAT TTA AAA TTT TTG  540
ACC GAG TAC GGC CCG TGT CGA CGT GGC GTT CAT ATC CCG AAT TGC GAT AAA AAA GGC TTC TAC AAA  600
AAC GTT TTA TCC CCG CGT CCG AGT AAG GGT CGT AAA CGA GGT TTT TGT TGG TGC GTT GAC AAA  660
AAG AAA CAA TGC CGT CCG TTG CCG GGT TAT ACT AAA GGC AAA GAA GAT GTT CAT TGT TAT TCT  720
TAC GGT CAA CCG TTG CCG GGT TAT ACT AAA GGC AAA GAA GAT GTT CAT TGT TAT TCT  780
ATG CAA TCT AAA TAA TGC ATC TCG AGA ATT C  811
```

ATGCAGGGGGCGGACCCACGCTCTCGGGCCGCTGCCTGACTCTGCTGGTGCTGCTCCCGCGGGCCGCCGGTGCCGCGGGCTGGC
MetGlnArgAlaArgProThrLeuTrpAlaAlaAlaLeuThrLeuLeuValLeuLeuArgGlyProProValAlaArgAlaGly
-1 +1

GCGAGCTCGGCGGGCTTGGGTCCCGTGGTGCGCTGCGAGCCGTGCGACGCGCCCTCCGCGCCCCGTGCGCGGAGCTG
AlaSerSerAlaGlyLeuGlyProValValArgCysAspAlaProSerAlaProProAlaValCysAlaGluLeu

GTGCGCGAGCCCGGGCTGCGGCTGCTGCTGACTGTGCGCACTGAGCGAGGGCCAGCCGTGCGGGCATCTACACCGAGCCTTCGCTGC
ValArgGluProGlyLeuArgLeuLeuLeuThrCysAlaLeuSerGlyHisLeuHisProCysGlyIleTyrThrGluProSerLeuLeuCys

CAGCCGTCGCCCGACGAGGCGCGACCGCTGCAGGCGCTCTGCTCAACGTAGTGCCTCAGCCGCTCGCCGCCCTACCTG
GlnProSerProAspGluAlaArgProLeuGlnAlaLeuLeuAspGlyArgGlyLeuCysValAsnAlaSerArgLeuArgAlaTyrLeu

CTGCCAGGCGCCCAGCTCCAGGAAATGCTAGTGAGTCGGAGGAAGACCGACCGCCAGGCCCGTCCGCAGTGTGGAGAGCCCGTCCGTCCAGCACGCACCGGGTG
LeuProAlaProProAlaProGlyAsnAlaSerGluSerGluAspArgSerAlaGlySerValGluSerProSerValSerSerThrHisArgVal

TCTGATCCCAAGTTCCACCCCTCCATTCAAAGATAATCATCATCAAGAAAGGGCATGCTAAAGACAGCCAGGCGCTACAAAGTTGACTACGAGTCTCAG
SerAspProLysPheHisProLeuHisSerLysIleIleIleIleLysLysGlyHisAlaLysAspSerGlnArgTyrLysValAspTyrGluSerGln

FIG. 15A

AGCACAGATACCCAGAACTTCTCCTCCGAGTCCCAAGCGGGAGACAGAATATGGTCCCTGCCGTAGAGAAATGGAAGACACACTGAATCACCTGAAGTTC
SerThrAspThrGlnAsnPheSerSerGluSerLysArgGluThrGluTyrGlyProCysArgArgGluMetGluAspThrLeuAsnHisLeuLysPhe

CTCAATGTGCTGAGTCCCAGGGGTGTACACACATTCCCAACTGTGACAAGAGAGGGATTTTATAAGAAAAAGCAGTGTGCCCTTCCAAAGGCAGGAAGCGG
LeuAsnValLeuSerProArgGlyValHisIleProAsnCysAspLysLysLysGlyPheTyrLysLysLysGlnCysArgProSerLysGlyArgLysArg

GGCTTCTGCTGGTGTGTGGATAAGTATGGGCAGCCTCTCCCAGGCTACACCACCAAGGGGAAGGGAGGACGTGCACTGCTACAGCATGCAGAGCAAGTAG
GlyPheCysTrpCysValAspLysTyrGlyGlnProLeuProGlyTyrThrThrLysGlyLysGlyGlyArgThrLysGlyLysGlyGlyArgThrLys.

FIG. 15B

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:

```
        (A) LENGTH: 70 amino acids
        (B) TYPE: amino acid
        (C) STRANDEDNESS: single
        (D) TOPOLOGY: linear (xi) SEQUENCE DESCRIPTION: SEQ ID NO:1:

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

(2) INFORMATION FOR SEQ ID NO:2:

(i) SEQUENCE CHARACTERISTICS:
        (A) LENGTH: 264 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 5
        (D) OTHER INFORMATION: /note= "There is natural
            heterogeneity at this position; Xaa can be glycine (Gly)
            or alanine (Ala)."

(xi) SEQUENCE DESCRIPTION: SEQ ID NO:2:

Gly Ala Ser Ser Xaa Gly Leu Gly Pro Val Arg Cys Glu Pro Cys
1               5                   10                  15

Asp Ala Arg Ala Leu Ala Gln Cys Ala Pro Pro Ala Val Cys Ala
            20                  25                  30

Glu Leu Val Arg Glu Pro Gly Cys Gly Cys Cys Leu Thr Cys Ala Leu
        35                  40                  45

Ser Glu Gly Gln Pro Cys Gly Ile Tyr Thr Glu Arg Cys Gly Ser Gly
    50                  55                  60

Leu Arg Cys Gln Pro Ser Pro Asp Glu Ala Arg Pro Leu Gln Ala Leu
65                  70                  75                  80

Leu Asp Gly Arg Gly Leu Cys Val Asn Ala Ser Ala Val Ser Arg Leu
            85                  90                  95

Arg Ala Tyr Leu Leu Pro Ala Pro Ala Pro Gly Asn Ala Ser Glu
        100                 105                 110

Ser Glu Glu Asp Arg Ser Ala Gly Ser Val Glu Ser Pro Ser Val Ser
    115                 120                 125

Ser Thr His Arg Val Ser Asp Pro Lys Phe His Pro Leu His Ser Lys
130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
            165                 170                 175

Ser Lys Arg Glu Thr Glu Tyr Gly Pro Cys Arg Arg Glu Met Glu Asp
        180                 185                 190

Thr Leu Asn His Leu Lys Phe Leu Asn Val Leu Ser Pro Arg Gly Val
    195                 200                 205
```

His Ile Pro Asn Cys Asp Lys Lys Gly Phe Tyr Lys Lys Gln Cys
    210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
                260

(2) INFORMATION FOR SEQ ID NO:3:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..792

(xi) SEQUENCE DESCRIPTION: SEQ ID NO:3:

```
ATG GGT GCA TCT TCT GCA GGT TTA GGT CCA GTT GTT CGT TGT GAA CCA      48
Met Gly Ala Ser Ser Ala Gly Leu Gly Pro Val Val Arg Cys Glu Pro
 1               5                  10                  15

TGT GAT GCT CGT GCT CTT GCT CAA TGT GCT CCA CCA GCT GTT TGT GCT      96
Cys Asp Ala Arg Ala Leu Ala Gln Cys Ala Pro Pro Ala Val Cys Ala
             20                  25                  30

GAA CTT GTT CGT GAA CCG GGT TGT GGT TGT TGT CTG ACT TGC GCA CTT     144
Glu Leu Val Arg Glu Pro Gly Cys Gly Cys Cys Leu Thr Cys Ala Leu
         35                  40                  45

TCT GAA GGT CAA CCA TGT GGT ATT TAT ACT GAA CGT TGT GGT TCT GGT     192
Ser Glu Gly Gln Pro Cys Gly Ile Tyr Thr Glu Arg Cys Gly Ser Gly
     50                  55                  60

CTG CGT TGT CAA CCA TCT CCA GAT GAA GCT CGT CCT CTG CAG GCT CTG     240
Leu Arg Cys Gln Pro Ser Pro Asp Glu Ala Arg Pro Leu Gln Ala Leu
 65                  70                  75                  80

CTG GAC GGT CGT GGT CTG TGC GTT AAC GCT TCC GCT GTT TCC CGT CTG     288
Leu Asp Gly Arg Gly Leu Cys Val Asn Ala Ser Ala Val Ser Arg Leu
                 85                  90                  95

CGC GCC TAC CTG CTG CCA GCG CCG CCA GCT CCA GGA AAT GCT AGT GAG     336
Arg Ala Tyr Leu Leu Pro Ala Pro Pro Ala Pro Gly Asn Ala Ser Glu
            100                 105                 110

TCG GAG GAA GAC CGC AGC GCC GGC AGT GTG GAG AGC CCG TCC GTC TCC     384
Ser Glu Glu Asp Arg Ser Ala Gly Ser Val Glu Ser Pro Ser Val Ser
        115                 120                 125

AGC ACG CAC CGG GTG TCT GAT CCC AAG TTC CAC CCC CTC CAT TCA AAG     432
Ser Thr His Arg Val Ser Asp Pro Lys Phe His Pro Leu His Ser Lys
    130                 135                 140

ATA ATC ATC ATC AAG AAA GGG CAT GCT AAA GAC AGC CAG CGC TAC AAA     480
Ile Ile Ile Ile Lys Lys Gly His Ala Lys Asp Ser Gln Arg Tyr Lys
145                 150                 155                 160

GTT GAC TAC GAG TCT CAG AGC ACA GAT ACC CAG AAC TTC TCC TCC GAG     528
Val Asp Tyr Glu Ser Gln Ser Thr Asp Thr Gln Asn Phe Ser Ser Glu
                165                 170                 175

TCC AAG CGG GAG ACA GAA TAT GGT CCC TGC CGT AGA GAA ATG GAA GAC     576
Ser Lys Arg Glu Thr Glu Tyr Gly Pro Cys Arg Arg Glu Met Glu Asp
            180                 185                 190

ACA CTG AAT CAC CTG AAG TTC CTC AAT GTG CTG AGT CCC AGG GGT GTA     624
Thr Leu Asn His Leu Lys Phe Leu Asn Val Leu Ser Pro Arg Gly Val
        195                 200                 205
```

```
CAC ATT CCC AAC TGT GAC AAG AAG GGA TTT TAT AAG AAA AAG CAG TGT       672
His Ile Pro Asn Cys Asp Lys Lys Gly Phe Tyr Lys Lys Lys Gln Cys
    210                 215                 220

CGC CCT TCC AAA GGC AGG AAG CGG GGC TTC TGC TGG TGT GTG GAT AAG       720
Arg Pro Ser Lys Gly Arg Lys Arg Gly Phe Cys Trp Cys Val Asp Lys
225                 230                 235                 240

TAT GGG CAG CCT CTG CCA GGC TAC ACC ACC AAG GGG AAG GAG GAC GTG       768
Tyr Gly Gln Pro Leu Pro Gly Tyr Thr Thr Lys Gly Lys Glu Asp Val
                245                 250                 255

CAC TGC TAC AGC ATG CAG AGC AAG TAG                                   795
His Cys Tyr Ser Met Gln Ser Lys
               260
```

(2) INFORMATION FOR SEQ ID NO:4:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Ala Ser Ser Ala Gly Leu Gly Pro Val Val Arg Cys Glu Pro
 1               5                  10                  15

Cys Asp Ala Arg Ala Leu Ala Gln Cys Ala Pro Pro Ala Val Cys Ala
                20                  25                  30

Glu Leu Val Arg Glu Pro Gly Cys Gly Cys Cys Leu Thr Cys Ala Leu
             35                  40                  45

Ser Glu Gly Gln Pro Cys Gly Ile Tyr Thr Glu Arg Cys Gly Ser Gly
         50                  55                  60

Leu Arg Cys Gln Pro Ser Pro Asp Glu Ala Arg Pro Leu Gln Ala Leu
65                  70                  75                  80

Leu Asp Gly Arg Gly Leu Cys Val Asn Ala Ser Ala Val Ser Arg Leu
                85                  90                  95

Arg Ala Tyr Leu Leu Pro Ala Pro Pro Ala Pro Gly Asn Ala Ser Glu
             100                 105                 110

Ser Glu Glu Asp Arg Ser Ala Gly Ser Val Glu Ser Pro Ser Val Ser
         115                 120                 125

Ser Thr His Arg Val Ser Asp Pro Lys Phe His Pro Leu His Ser Lys
     130                 135                 140

Ile Ile Ile Ile Lys Lys Gly His Ala Lys Asp Ser Gln Arg Tyr Lys
145                 150                 155                 160

Val Asp Tyr Glu Ser Gln Ser Thr Asp Thr Gln Asn Phe Ser Ser Glu
                165                 170                 175

Ser Lys Arg Glu Thr Glu Tyr Gly Pro Cys Arg Arg Glu Met Glu Asp
             180                 185                 190

Thr Leu Asn His Leu Lys Phe Leu Asn Val Leu Ser Pro Arg Gly Val
         195                 200                 205

His Ile Pro Asn Cys Asp Lys Lys Gly Phe Tyr Lys Lys Lys Gln Cys
     210                 215                 220

Arg Pro Ser Lys Gly Arg Lys Arg Gly Phe Cys Trp Cys Val Asp Lys
225                 230                 235                 240

Tyr Gly Gln Pro Leu Pro Gly Tyr Thr Thr Lys Gly Lys Glu Asp Val
                245                 250                 255

His Cys Tyr Ser Met Gln Ser Lys
               260
```

(2) INFORMATION FOR SEQ ID NO:5:

(i) SEQUENCE CHARACTERISTICS:
        (A) LENGTH: 811 base pairs
        (B) TYPE: nucleic acid
        (C) STRANDEDNESS: single
        (D) TOPOLOGY: linear (xi) SEQUENCE DESCRIPTION: SEQ ID NO:5:

```
GGTGCTTCTT CTGCTGGTCT TGGACCAGTT GTTCGTTGTG AACCATGTGA TGCACGAGCT      60

TTAGCTCAAT GTGCTCCACC ACCAGCTGTT TGTGCTGAAT TAGTTCGAGA ACCAGGTTGT     120

GGTTGTTGTT TAACTTGTGC TTTATCTGAA GGTCAACCAT GTGGTATTTA TACTGAACGT     180

TGCGGTAGTG GTTTGCGTTG TCAACCAAGC CCAGATGAAG CTAGGCCTTT ACAAGCATTA     240

TTAGATGGTC GAGGTCTGTG TGTTAATGCG TCCGCTGTTT CTCGATTGCG CGCTTATTTA     300

TTACCTGCCC CACCGGCACC GGGTAACGCC TCCGAAAGCG AAGAGGATCG TTCTGCGGGT     360

TCCGTTGAAT CTCCAAGTGT GAGTTCTACC CATCGAGTTA GCGACCCGAA ATTTCATCCG     420

TTGCACTCTA AAATCATTAT TATTAAAAAG GGTCACGCAA AGGATTCTCA ACGTTATAAG     480

GTGGATTATG AAAGCCAATC TACCGACACT CAAAATTTTA GTAGTGAAAG TAAACGTGAA     540

ACCGAGTACG GCCCGTGTCG ACGTGAGATG GAGGATACCT TAAACCATTT AAAATTTTTG     600

AACGTTTTAT CCCCGCGTGG CGTTCATATC CCGAATTGCG ATAAAAAAGG CTTCTACAAA     660

AAGAAACAAT GCCGTCCGAG TAAGGGTCGT AAACGAGGTT TTTGTTGGTG CGTTGACAAA     720

TACGGTCAAC CGTTGCCGGG TTATACTACT AAAGGCAAAG AAGATGTTCA TTGTTATTCT     780

ATGCAATCTA AATAATGCAT CTCGAGAATT C                                    811
```

(2) INFORMATION FOR SEQ ID NO:6:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..873

(xi) SEQUENCE DESCRIPTION: SEQ ID NO:6:

```
ATG CAG CGG GCG CGA CCC ACG CTC TGG GCC GCT GCG CTG ACT CTG CTG       48
Met Gln Arg Ala Arg Pro Thr Leu Trp Ala Ala Ala Leu Thr Leu Leu
265             270                 275                 280

GTG CTG CTC CGC GGG CCG CCG GTG GCG CGG GCT GGC GCG AGC TCG GCG       96
Val Leu Leu Arg Gly Pro Pro Val Ala Arg Ala Gly Ala Ser Ser Ala
                285                 290                 295

GGC TTG GGT CCC GTG GTG CGC TGC GAG CCG TGC GAC GCG CGT GCA CTG      144
Gly Leu Gly Pro Val Val Arg Cys Glu Pro Cys Asp Ala Arg Ala Leu
            300                 305                 310

GCC CAG TGC GCG CCT CCG CCC GCC GTG TGC GCG GAG CTG GTG CGC GAG      192
Ala Gln Cys Ala Pro Pro Pro Ala Val Cys Ala Glu Leu Val Arg Glu
        315                 320                 325

CCG GGC TGC GGC TGC TGC CTG ACG TGC GCA CTG AGC GAG GGC CAG CCG      240
Pro Gly Cys Gly Cys Cys Leu Thr Cys Ala Leu Ser Glu Gly Gln Pro
    330                 335                 340

TGC GGC ATC TAC ACC GAG CGC TGT GGC TCC GGC CTT CGC TGC CAG CCG      288
Cys Gly Ile Tyr Thr Glu Arg Cys Gly Ser Gly Leu Arg Cys Gln Pro
345                 350                 355                 360

TCG CCC GAC GAG GCG CGA CCG CTG CAG GCG CTG CTG GAC GGC CGC GGG      336
Ser Pro Asp Glu Ala Arg Pro Leu Gln Ala Leu Leu Asp Gly Arg Gly
                365                 370                 375
```

```
CTC TGC GTC AAC GCT AGT GCC GTC AGC CGC CTG CGC GCC TAC CTG CTG        384
Leu Cys Val Asn Ala Ser Ala Val Ser Arg Leu Arg Ala Tyr Leu Leu
            380                 385                 390

CCA GCG CCG CCA GCT CCA GGA AAT GCT AGT GAG TCG GAG GAA GAC CGC        432
Pro Ala Pro Ala Pro Ala Pro Gly Asn Ala Ser Glu Ser Glu Glu Asp Arg
        395                 400                 405

AGC GCC GGC AGT GTG GAG AGC CCG TCC GTC TCC AGC ACG CAC CGG GTG        480
Ser Ala Gly Ser Val Glu Ser Pro Ser Val Ser Ser Thr His Arg Val
        410                 415                 420

TCT GAT CCC AAG TTC CAC CCC CTC CAT TCA AAG ATA ATC ATC ATC AAG        528
Ser Asp Pro Lys Phe His Pro Leu His Ser Lys Ile Ile Ile Ile Lys
425                 430                 435                 440

AAA GGG CAT GCT AAA GAC AGC CAG CGC TAC AAA GTT GAC TAC GAG TCT        576
Lys Gly His Ala Lys Asp Ser Gln Arg Tyr Lys Val Asp Tyr Glu Ser
            445                 450                 455

CAG AGC ACA GAT ACC CAG AAC TTC TCC TCC GAG TCC AAG CGG GAG ACA        624
Gln Ser Thr Asp Thr Gln Asn Phe Ser Ser Glu Ser Lys Arg Glu Thr
        460                 465                 470

GAA TAT GGT CCC TGC CGT AGA GAA ATG GAA GAC ACA CTG AAT CAC CTG        672
Glu Tyr Gly Pro Cys Arg Arg Glu Met Glu Asp Thr Leu Asn His Leu
        475                 480                 485

AAG TTC CTC AAT GTG CTG AGT CCC AGG GGT GTA CAC ATT CCC AAC TGT        720
Lys Phe Leu Asn Val Leu Ser Pro Arg Gly Val His Ile Pro Asn Cys
490                 495                 500

GAC AAG AAG GGA TTT TAT AAG AAA AAG CAG TGT CGC CCT TCC AAA GGC        768
Asp Lys Lys Gly Phe Tyr Lys Lys Lys Gln Cys Arg Pro Ser Lys Gly
505                 510                 515                 520

AGG AAG CGG GGC TTC TGC TGG TGT GTG GAT AAG TAT GGG CAG CCT CTC        816
Arg Lys Arg Gly Phe Cys Trp Cys Val Asp Lys Tyr Gly Gln Pro Leu
            525                 530                 535

CCA GGC TAC ACC ACC AAG GGG AAG GAG GAC GTG CAC TGC TAC AGC ATG        864
Pro Gly Tyr Thr Thr Lys Gly Lys Glu Asp Val His Cys Tyr Ser Met
        540                 545                 550

CAG AGC AAG TAG                                                         876
Gln Ser Lys
        555
```

(2) INFORMATION FOR SEQ ID NO:7:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:7:

```
Met Gln Arg Ala Arg Pro Thr Leu Trp Ala Ala Leu Thr Leu Leu
1               5                   10                  15

Val Leu Leu Arg Gly Pro Pro Val Ala Arg Ala Gly Ala Ser Ser Ala
            20                  25                  30

Gly Leu Gly Pro Val Val Arg Cys Glu Pro Cys Asp Ala Arg Ala Leu
        35                  40                  45

Ala Gln Cys Ala Pro Pro Ala Val Cys Ala Glu Leu Val Arg Glu
    50                  55                  60

Pro Gly Cys Gly Cys Cys Leu Thr Cys Ala Leu Ser Glu Gly Gln Pro
65                  70                  75                  80

Cys Gly Ile Tyr Thr Glu Arg Cys Gly Ser Gly Leu Arg Cys Gln Pro
            85                  90                  95
```

```
Ser Pro Asp Glu Ala Arg Pro Leu Gln Ala Leu Leu Asp Gly Arg Gly
            100                 105                 110

Leu Cys Val Asn Ala Ser Ala Val Ser Arg Leu Arg Ala Tyr Leu Leu
        115                 120                 125

Pro Ala Pro Pro Ala Pro Gly Asn Ala Ser Glu Ser Glu Glu Asp Arg
        130                 135                 140

Ser Ala Gly Ser Val Glu Ser Pro Ser Val Ser Ser Thr His Arg Val
145                 150                 155                 160

Ser Asp Pro Lys Phe His Pro Leu His Ser Lys Ile Ile Ile Ile Lys
                165                 170                 175

Lys Gly His Ala Lys Asp Ser Gln Arg Tyr Lys Val Asp Tyr Glu Ser
                180                 185                 190

Gln Ser Thr Asp Thr Gln Asn Phe Ser Ser Glu Ser Lys Arg Glu Thr
        195                 200                 205

Glu Tyr Gly Pro Cys Arg Arg Glu Met Glu Asp Thr Leu Asn His Leu
        210                 215                 220

Lys Phe Leu Asn Val Leu Ser Pro Arg Gly Val His Ile Pro Asn Cys
225                 230                 235                 240

Asp Lys Lys Gly Phe Tyr Lys Lys Lys Gln Cys Arg Pro Ser Lys Gly
                245                 250                 255

Arg Lys Arg Gly Phe Cys Trp Cys Val Asp Lys Tyr Gly Gln Pro Leu
                260                 265                 270

Pro Gly Tyr Thr Thr Lys Gly Lys Glu Asp Val His Cys Tyr Ser Met
        275                 280                 285

Gln Ser Lys
        290
```

IGF/IGFBP COMPLEX FOR PROMOTING BONE FORMATION AND FOR REGULATING BONE REMODELING

This application is a continuation of U.S. patent application Ser. No. 08/806,918, filed Feb. 26, 1997, now abandoned, which is a continuation of U.S. patent application Ser. No 08/450,258, filed May 25, 1995, now abandoned, which is a continuation of U.S. patent application Ser. No. 08/278,456, filed Jul. 20, 1994, now abandoned, each of which is incorporated by reference in its entirety.

TECHNICAL FIELD

The instant invention relates generally to polypeptide factors and their use in bone growth and maturation. Specifically, the invention relates to the use of a complex of insulin-like growth factor (IGF) and insulin-like growth factor binding protein (IGFBP) with or without an inhibitor of bone resorption to stimulate bone formation.

BACKGROUND ART

Growth factors are polypeptides which stimulate a wide variety of biological responses (e.g., DNA synthesis, cell division, cell differentiation, expression of specific genes, etc.) in a defined population of target cells. A variety of growth factors have been identified including transforming growth factor-$\beta1$ (TGF-$\beta1$), TGF-$\beta2$, TGF-$\beta3$, epidermal growth factor (EGF), plotelet-derived growth factor (PDGF), fibroblast growth factor (FGF), insulin-like growth factor-I (IGF-I), and IGF-II.

IGF-I and IGF-II are related in amino acid sequence and structure, with each polypeptide having a molecular weight of approximately 7500 daltons. IGF-I mediates the major effects of growth hormone and thus is the primary mediator of skeletal growth after birth. IGF-I has also been implicated in the actions of various other growth factors, since treatment of cells with such growth factors leads to increased production of IGF-I. Both IGF-I and IGF-II have insulin-like activity (hence the name) and are mitogenic (stimulating cell division) for various types of cells involved in the growth and differentiation of skeletal tissues such as muscle and bone, as well as non-skeletal tissues.

IGF can be measured in blood serum to diagnose abnormal growth-related conditions, e.g., gigantism, acromegaly, dwarfism, various growth hormone deficiencies, etc. Although IGF is produced in many tissues, most circulating IGF is believed to be synthesized in the liver.

Unlike most growth factors, the IGFs are present in substantial quantity in the circulation, but only a very small fraction of this IGF is free in the circulation or in other body fluids. Most IGF is complexed with IGF-binding proteins. IGF in the blood is mainly complexed with IGFBP-3, the major circulating IGF-binding protein. Almost all IGF circulates in a non-covalently associated ternary complex composed of IGF-I or -II, an IGF specific binding protein termed IGFBP-3, and a larger protein termed the Acid Labile Subunit (ALS). This ternary complex is composed of equimolar amounts of each of the three components. The ALS has no direct IGF binding activity and appears to bind only a pre-formed IGF/IGFBP-3 complex. The ternary complex of IGF+IGFBP-3+ALS has a molecular weight of approximately 150,000 daltons. This ternary complex likely functions in the circulation "as a reservoir and a buffer for IGF-I and IGF-II preventing rapid changes of free IGF." Blum, W. F., et al., "Plasma IGFBP-3 Levels as Clinical Indicators", In *Modern Concepts in Insulin-Like Growth Factors*, E. M. Spencer, ed., Elsevier, N.Y., pages 381–393, 1991.

Having most circulating IGF in complexes is beneficial. Excess free IGF can cause serious hypoglycemia because IGF has insulin-like effects on circulating glucose levels. In contrast to the low levels of free IGFs and IGFBP-3, there is a substantial pool of free ALS in plasma which assures that IGF/IGFBP-3 complex entering the circulation immediately forms a ternary complex.

IGF Binding Proteins

IGFBP-3 is the most abundant IGF binding protein in the circulation. Recently, Wood et al. (*Mol. Endocrin.* (1988), 2:1176–85) and Spratt et al. (*Growth Factors* (1990), 3:63–72) described the cloning and expression of human IGFBP-3, whose structure is incorporated herein by reference. The gene for IGFBP-3 codes for 291 amino acids, the first 27 of which represent a characteristic signal sequence. Thus, the mature protein comprises 264 amino acids and has a predicted molecular weight of 28,749 (without glycosylation or other post-translational changes). When the human IGFBP-3 gene was expressed in Chinese hamster ovary ("CHO") cells and the conditioned culture medium was subjected to SDS electrophoresis and transferred to nitrocellulose membrane for ligand binding analysis, Spratt et al. reported "the presence of a 43–45 kd doublet, a 28 kd band and a minor 31 kd band" protein bands (p. 69), indicating there were post-translational changes. A side-by-side comparison revealed that the 43–45 kd doublet was also present in human serum.

FIGS. 12–15 show coding sequences and deduced amino acid sequences of IGFBP-3 suitable for various forms of use in the present invention.

It is unclear which tissue is the primary source of circulating IGFBP-3, although synthesis has been demonstrated in numerous cell types, including human fibroblasts, liver cells (most likely Kupfer cells) and osteoblasts. cDNA libraries that include the IGFBP-3 cDNA have been obtained from liver and other tissues. Vascular endothelial cells produce IGFBP-3 and may be the major source for systemic IGFBP-3.

IGFBP-3 has been purified from natural sources and produced by recombinant means. For instance, IGFBP-3 can be purified from natural sources using a process such as that shown in Martin and Baxter (*J. Biol. Chem.* (1986) 261:8754–60) IGFBP-3 also can be synthesized by recombinant organisms as discussed in Sommer, A. et al., In *Modern Concepts of Insulin-Like Growth Factors*, E. M. Spencer, ed., Elsevier, N.Y., pp. 715–728, 1991. This recombinant IGFBP-3 binds IGF-I with a 1:1 molar stoichiometry.

At least five other distinct IGF binding proteins have been identified in various tissues and body fluids. Although all these proteins bind IGFs, they each originate from separate genes and they have distinct amino acid sequences. Thus, the binding proteins are not merely analogs of a common precursor. For example, Spratt et al. compared the amino acid sequences of IGFBP-1, -2 and -3. Of the total 264 amino acids in the mature protein, only 28% of the amino acids are identical between IGFBP-3 and IGFBP-1, and 33% are identical between IGFBP-3 and IGFBP-2. Spratt et al. suggested that the similar portions of the binding proteins are the region(s) that bind IGF. Unlike IGFBP-3, the other IGFBPs in the circulation are not saturated with IGFs. All six known IGFBPs are reviewed and compared by Shimasaki and Ling, *Prog. Growth Factor Res.* (1991) 3:243–66.

Spencer et al. (1991) *Bone* 12:21–26; and Tobias et al. (1992) *Endocrinology* 131:2387–2392 report the stimulation of-bone formation by IGF-I.

The trabecular bone of rats, like that of humans, shows a coupling of bone formation to bone resorption, such that the increased resorption that occurs with estrogen deficiency entrains increased bone formation, which can be suppressed by inhibition of bone resorption. It has been established that in adult humans this coupling of formation and resorption involves a site specific sequence of events, in which bone resorption is normally followed, at the same site, by bone formation. Frost (1985) *Clin. Orthop. Rel. Res.* 200:198–225.

There is also some evidence that bone formation can occur without previous bone resorption, primarily in those situations where demands for mechanical support of the skeleton are increased (modeling). Parfitt, A. M., et al. (1984) *Calcif. Tissue Int.* 36:5123–5128.

The present invention offers in vivo single or combination therapy for stimulating new bone formation through the administration of the IGF/IGFBP complex or through the administration of the IGF/IGFBP complex and an agent which inhibits bone resorption. These combinations provide more effective therapy for prevention of bone loss and replacement of bone.

DISCLOSURE OF THE INVENTION

The present invention discloses the use of IGF and its binding protein for the initiation and promotion of bone formation and the regulation of bone remodeling. The IGF/IGFBP-3 complex can be used alone or in conjunction with an inhibitor of bone resorption.

The present invention discloses a method for stimulating bone formation in a subject who has a bone marrow disorder causing bone loss. The method comprises administering to the subject pharmaceutically effective doses of IGF-I and IGFBP-3, with or without an inhibitor of bone resorption.

In another embodiment, the present invention discloses a method for stimulating bone formation in a subject who has a connective tissue disorder causing bone loss. The method comprises administering to the subject pharmaceutically effective doses of the IGF-I/IGFBP-3 complex.

In another embodiment, the present invention discloses a method for treating a subject who has drug-related osteoporosis. The method comprises administering to the subject pharmaceutically effective doses of the IGF-I/IGFBP-3 complex.

In another embodiment, the present invention discloses a method of stimulating bone formation in a subject who has bone loss due to pregnancy, lactation, chronic hypophosphatemia, hyperphosphatasia, insulin-dependent diabetes mellitus, anorexia nervosa, cadmium poisoning, juvenile osteoporosis. The method comprises administering to the subject pharmaceutically effective doses of the IGF-I/IGFBP-3 complex.

In another embodiment, the present invention discloses a method for stimulating bone formation in a subject who has periodontal bone loss. The method comprises administering to the subject pharmaceutically effective doses of IGF-I and IGFBP-3.

In another embodiment, the present invention discloses a method for stimulating bone formation in a subject who has bone loss associated with osteoarthritis, disuse, or prolonged exposure to reduced gravitational field. The method comprises administering to the subject pharmaceutically effective doses of IGF-I and IGFBP-3.

In another embodiment, the present invention discloses a composition for inducing bone formation in a subject. The composition comprises IGF-I, IGFBP-3 and an inhibitor of bone resorption in a pharmaceutically acceptable excipient.

BRIEF DESCRIPTION OF THE FIGURES

FIGS. 2A and 2B show bar graphs of mean body weights (2A) and lean body mass (2B) of ovariectomized (OVX) animals treated for 8 weeks with rhIGF-I or rhIGF1/IGFBP-3 complex at the doses of IGF-I indicated, compared to no treatment (solid bars) and sham operated controls (solid line);

FIG. 3 shows a bar graph of endochondral bone growth) of ovariectomized (OVX) animals treated for 8 weeks with rhIGF-I or rhIGF-I/IGFBP-3 complex at the doses of IGF-I indicated, compared to no treatment (solid bars) and sham operated controls (solid line);

FIGS. 7A–7D show bar graphs of bone formation rates of cancellous bone in the metaphyses (7A), epiphyses (7B), lumbar vertebral bodies (7C) and femoral neck region (7D), of ovariectomized (OVX) animals treated for 8 weeks with rhIGF-I or rhIGF-I/IGFBP-3 complex with the doses of IGF-I indicated, compared to no treatment (solid bars) and sham operated controls (solid line), where an asterisk indicates $p<0.05$ compared to OVX group;

FIG. 11 shows the amino acid sequences of human IGF-I used in the present invention (SEQ ID NO:1);

FIG. 12 shows the amino acid sequence of human IGFBP-3 (SEQ ID NO:2), where an asterisk at position 5 indicates substitution of glycine for alanine according to naturally occurring heterogeneity in the sequence (SEQ ID NO:2);

FIG. 13 shows a nucleotide sequence of human IGFBP-3 (SEQ ID NO:3–4) used to produce rhIBFBP-3 for use in accordance with the invention;

FIG. 14 shows an alternate nucleotide sequence (SEQ ID NO:5) for production of rhIBFBP-3 for use in accordance with the invention; and FIG. 15 shows a second alternate nucleotide sequence (SEQ ID NO:6–7) for production of rhIGFBP-3 for use in accordance with the invention.

MODES FOR CARRYING OUT THE INVENTION

A. Definitions

Figure 1:
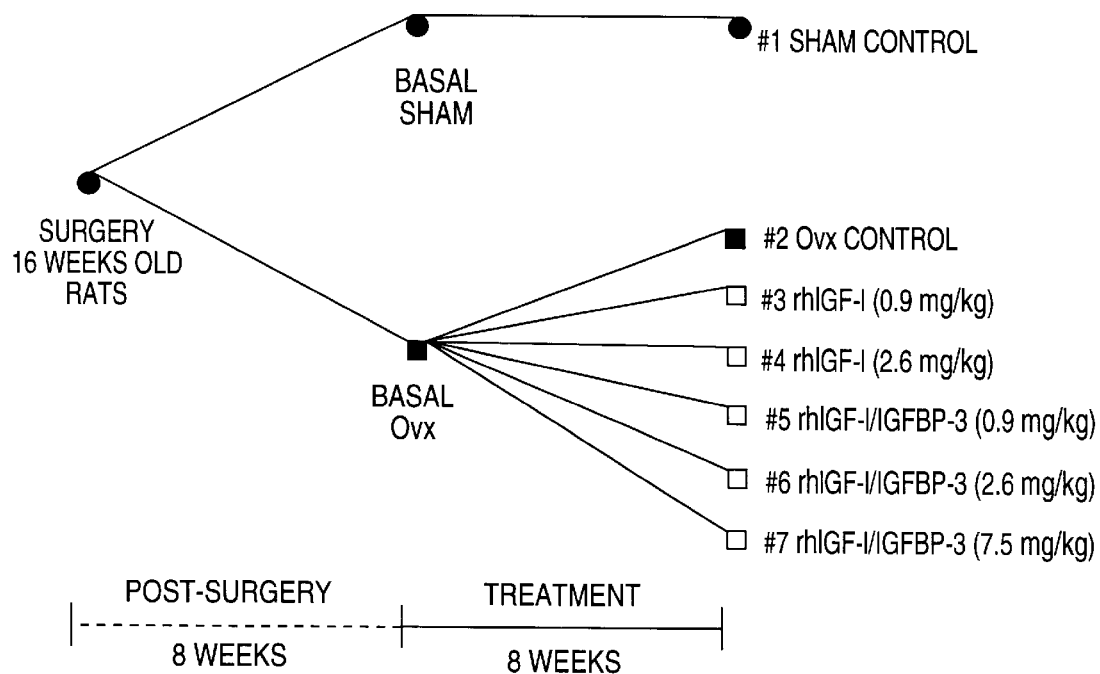
FIG. 1 shows a schematic of the experimental design used in experiments carried out in support of the invention (Example 2)

It must be noted that as used in this specification and the appended claims, the singular forms "a", "an" and "the" include plural referents unless the context clearly dictates otherwise.

The term "connective tissue disorder" includes conditions such as osteogenesis imperfecta, Ehlers-Danlos syndrome, Marfans syndrome, cutis laxa, homocystinuria, Mankes's syndrome and scurvy. These have been reported to be associated with and cause bone loss.

"Drug-related osteoporosis" means osteoporosis whose only identified cause is a drug. The definition includes all known drugs which cause osteoporosis, as well as those drugs later discovered to cause osteoporosis. Examples of drugs known to cause osteoporosis include corticosteroids, heparin, oral anticoagulants, anticonvulsants, methotrexate, thyroid hormone, lithium and gonadotrophin-releasing analogs.

"Insulin-like growth factor (IGF)" comprises a family of factors, including but not limited to IGF-I and IGF-II. IGF is a polypeptide having a molecular weight of about 7500 daltons. IGF can be obtained from natural sources or prepared by recombinant means. Preferably IGF is IGF-I from human sources. Most preferably, IGF is human IGF-I made by recombinant means, such as by the methods detailed in Example 3 herein, and designated rhIGF-I.

"Insulin-like growth factor binding protein (IGFBP)" comprises a family of binding proteins, including but not limited to IGFBP-1, IGFBP-2, IGFBP-3, IGFBP-4, IGFBP-5 and IGFBP-6. Each IGFBP can be obtained from natural sources or prepared by recombinant means, such as detailed in Example 4 herein. At least one form of IGFBP (for example, IGFBP-3) complexes with IGF and with a third molecule known as ALS. IGFBP also can be a mixture of any combination of the six IGFBP's. Such a mixture would take advantage of the different binding affinities for IGF-I and/or IGF-II, the ability of some IGFBP's to bind to cell surfaces, and the different half-lives.

A "therapeutic composition" as used herein is defined as comprising the IGF binding protein (IGFBP) with IGF and a bone resorption inhibitor. The therapeutic composition can also contain excipients such as water, minerals and carriers such as protein.

The method of the present invention contemplates treating a subject in need of local bone repair or replacement with IGFBP in combination with IGF with or without a bone resorption inhibitor. The IGF may be any of the IGF family, including but not limited to, IGF-I and IGF-II, or a combination thereof. When IGF-I and IGF-II are combined, the ratio of IGF-I to IGF-II ranges from 0.01:1 to 99:1.

"IGFBP-1" is an IGF-binding protein whose molecular structure was disclosed by Brewer et al., *Biochem. Biophys. Res. Comm.* (1988) 152(3):1289–1297, and by Drop et al. in PCT Publication No. WO 89/98667, published on Sep. 21, 1989, and is incorporated herein by reference. Human IGFBP-1 has 234 amino acids and a molecular weight of about 28 kd.

"IGFBP-2" comprises 289 amino acids (human) and has a molecular weight of 36 kd under nonreducing conditions. The amino acid sequence of human IGFBP-2 was determined from cDNA clones isolated from a human fetal liver library by Binkert et al. *EMBO J.* (1989) 8:2493–2502, and is incorporated herein by reference. IGFBP-2 also may bind to cell surfaces. IGFBP-2 has a preference for IGF-II, and thus is preferred in formulations comprising IGF-II.

"IGFBP-3" is the preferred IGFBP in the IGF/IGFBP complex. Native and recombinant IGFBP-3, as well as some N-terminal and C-terminal fragments, bind IGF-I and IGF-II. Human IGFBP-3 comprises 264 amino acids and has three potential N-linked glycosylation sites. IGFBP-3 is the major IGFBP in blood.

Nearly all IGF-I or IGF-II in blood is bound to IGFBP-3. The IGF/IGFBP-3 complex normally circulates in the form of a complex in humans and other mammals and avians. This complex associates with a third protein (ALS), which is present in excess over the concentration of IGF and IGFBP-3. Therefore, in the circulation, ALS is found both associated with the IGF/IGFBP-3 complex and in free form. The resultant ternary complex has a size of about 150 kD. Administration of a pre-formed complex of IGF and IGFBP-3, either from natural or recombinant sources, results in the formation of the ternary complex with the normally excess ALS. This type of treatment appears to produce a long term increase in the level of circulating IGF, which is gradually released from the ternary complex. This mode of administration avoids the detrimental side effects associated with administration of free IGF-I, e.g., hypoglycemia, suppression of growth hormone and ALS production, and release of endogenous IGF-II since administered exogenous free IGF-I replaces endogenous IGF-II in normally circulating IGF-II/IGFBP-3 complexes.

"IGFBP-4" and "IGFBP-6" are glycosylated proteins which are widely distributed in the body. The primary structure of IGFBP-4 was reported by Shimasaki et al. *Mol. Endocrinol.* (1990) 4:1451–1458, and is incorporated herein by reference. IGFBP-6, whose cDNA has been isolated by Shimasaki et al. (*Mol. Endocrinol.* (1991) 5:938–48), has a much greater affinity for IGF-II than for IGF-I and may be preferred with formulations containing IGF-II. This reference is incorporated herein by reference.

"IGFBP-5" is a 252-amino acid protein which is not glycosylated. Shimasaki et al. (*J. Biol. Chem.* (1991) 266:10646–53) cloned human IGFBP-5 cDNA from a human placenta library, and is incorporated herein by reference.

Depending on the binding, metabolic and pharmacokinetic characteristics required in the IGF/IGFBP complex formulation, these binding proteins can be added to the complex formulation in various proportions. These IGFBP's can be combined in a wide variety of ratios with IGF-I and/or IGF-II.

The term "inhibition of bone resorption" refers to prevention of bone loss, especially the inhibition of removal of existing bone either from the mineral phase and/or the organic matrix phase, through direct or indirect alteration of osteoclast formation or metabolism. Thus, the term "inhibitor of bone resorption" as used herein refers to agents that prevent bone loss by the direct or indirect alteration of osteoclast formation or metabolism.

The term "bone remodeling" refers to that process which renews the skeleton and repairs microdamage before it accumulates to the point of loss of skeletal integrity. Most adult human metabolic bone disease results from derangement of remodeling processes. The individual remodeling packets are known as "basic multicellular units" (BMU). Remodeling which occurs in. BMUs follows a preprogrammed sequence: activation→resorption→formation (ARF). (Recker, R. R., "Bone Histomorphometry: Techniques and Interpretation." Boca Raton, Fla., 1983, pp. 37–57.)

"Bone formation" includes increases in the number and/or activity of BMU (Basic Multicellular Units) producing new bone. This process can take place anywhere in the skeleton and affect cancellous and/or cortical bone with no regard to functional differences and turn-over rates which particular bone sites might have in the skeleton. (Frost (1986) *Intermediary Organization of the Skeleton. Vols. I and II*. CRC Press, Boca Raton, Fla.)

The term "osteogenically effective" means that amount which affects the formation and differentiation of mature bone or early bone progenitor cells. As used herein, an osteogenically effective dose is also "pharmaceutically effective."

The term "subject" as used herein refers to a living vertebrate animal such as a mammal or bird in need of treatment, i.e., in need of bone repair or replacement. Such need arises in connective tissue disorders such as osteogenesis imperfecta, Ehlers-Danlos syndrome, Marfans syndrome, cutis laxa, homocystinuria, Menkes's syndrome and scurvy; osteoporosis related to such drugs as corticosteroids, heparin, oral anticoagulants, anticonvulsants, methotrexate, thyroid hormone, lithium and gonadotrophin-releasing analogs; pregnancy; lactation; chronic hypophosphatemia; hyperphosphatasia; insulin-dependent diabetes mellitus; anorexia nervosa; Paget's disease of bone; cadmium poisoning; periodontal disease; osteoarthritis, disuse of the musculoskeletal system such as occurs during prolonged bed rest, paralysis or semi-paralysis; and prolonged exposure to reduced gravitational field.

The term "treatment" as used herein shall mean (1) providing a subject with an amount of a substance sufficient to act prophylactically to prevent the development of bone loss; or (2) providing a subject with a sufficient amount of a substance so as to alleviate or eliminate the problems associated with the bone loss.

B. General methods

Drugs which prevent bone loss and/or add back lost bone have been evaluated in the ovariectomized rat. This animal model is well established in the art (see, for example, Wronski et al. (1985) *Calcif. Tissue Int*. 37:324–328; Kimmel et al. (1990) *Calcif. Tissue Int*. 46:101–110; Durbridge et al. (1990) *Calcif. Tissue Int*. 47:383–387; and Miller et al. (1991) *Bone* 12:439–446; these references are hereby incorporated in their entirety). Wronski et al. ((1985) *Calcif. Tissue Int*. 43:179–183)) describe the association of bone loss and bone remodeling in the ovariectomized rat.

Examples of inhibitors of bone resorption include estrogen, such as conjugated estrogen, tamoxifen, bisphosphonates, calcitonins, or other small peptides or molecules that may inhibit bone resorption. (Turner et al. (1987) *J. Bone Mineral Res*. 2:115–122; Wronski et al. (1988) *Endocrinology* 128:681–686; and Wronski et al. (1989) *Endocrinology* 125:810–816; Pfeilshifter et al. (1987) *Proc. Natl. Acad. Sci. U.S.A*. 84:2024–2028; Turner et al. (1988) *Endocrinology* 122:1146–1150). An example of a small peptide is echistatin, which includes the arginine-glycine-aspartate (RGD) sequence which is recognized by some cell surface adhesion receptors and apparently disrupts osteoclast interaction (Fisher et al. (1993) *Endocrinology* 132: 1411–13). Another example of a bone resorption factor is OPF or osteoclastpoietic factor (PCT Publication WO 93/01827 published Feb. 4, 1993). Other agents that are under investigation or have been proposed to inhibit bone resorption include mithramycin, gallium nitrate, glucocorticoids, transforming growth factor-$\beta$ (TGF-$\beta$), interferon-$\gamma$ and amylin. (Zaidi et al. (October 1992) *Curr. Opin. Therapeutic Patents*, pp. 1517–38).

The entire molecule of a particular inhibitor may be used, or alternatively, only a functional part of the inhibitor molecule may be used. Bisphosphonates include, but are not limited to, pamidronate acid, alendronate, tiludronate, risedronate and other experimental compounds.

Certain growth factors can inhibit bone resorption, or are anti-resorptive. Examples of such growth factors include but are not limited to the transforming growth factors-$\beta$.

In accordance with the method of the present invention, the formulation comprises a complex of IGF and IGFBP administered with or without a bone resorption inhibitor.

Preferably, the IGF is IGF-I, although IGF-II can be useful. Preferably, the IGFBP is IGFBP-3. Because IGF and IGFBP-3 naturally bind in a 1:1 molar ratio, a composition of equimolar amounts of IGF and IGFBP-3 is preferred. Nevertheless, the composition can be formulated with IGF:IGFBP-3 molar ratios ranging from 0.5:1 to 1.5:1. More preferably, the molar ratio is 0.9:1 to 1.3:1; and most preferably, the composition is formulated with approximately a 1:1 molar ratio.

In accordance with the method of the present invention, IGF and IGFBP-3 are human proteins obtained from natural or recombinant sources. Most preferably, IGF and IGFBP-3 are human IGF-I and IGFBP-3 made by recombinant means and designated rhIGF-I and rhIGFBP-3, respectively. rhIGFBP-3 can be in glycosylated or non-glycosylated form. *E. coli* is a source of the non-glycosylated IGFBP-3. Glycosylated IGFBP-3 can be obtained from CHO-cells.

The method of the present invention provides for formulating the complex in modes which are readily apparent to those skilled in the art. Preferably, the IGF and IGFBP-3 are complexed prior to administration to the treated individual. Preferably, the complex is formed by mixing approximately equimolar amounts of IGF-I and IGFBP-3 dissolved in physiologically compatible carriers such as normal saline solution or phosphate buffered saline solution. Most preferably, a concentrated solution of rhIGF-I and a concentrated solution of IGFBP-3 are mixed together for a sufficient time to form an equimolar complex.

Pharmaceutical compositions of the invention which include IGF, IGFBP and an inhibitor of bone resorption for administration include osteogenically effective amounts of IGF and IGFBP to promote bone formation and an inhibitory amount of a bone resorption inhibitor, in addition to a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, plasma, other protein-containing solutions and the like. These compositions may optionally include stabilizers, antioxidants, antimicrobials, preservatives, buffering agents, surfactants, and other accessory additives. The IGF/IGFBP complex and inhibitor of bone resorption may also be delivered in a slow release form from a suitable carrier.

Various vehicles may be used with the present invention. A thorough discussion of suitable vehicles for parenteral administration may be found in E. W. Martin, "Remington's Pharmaceutical Sciences" (Mack Pub. Co., current edition). Sections relating to the excipient vehicles and formulating are incorporated herein by reference. Such formulations are generally known to those skilled in the art and are administered systemically to provide systemic treatment.

The IGF/IGFBP complex and an agent which inhibits bone resorption may be administered simultaneously, as a single composition to the subject, or sequentially. If administered sequentially, the period between the administration of the IGF/IGFBP complex and the inhibitor of bone resorption is typically one day to one year, and preferably, one week to six months. If the IGF/IGFBP complex and the agent which inhibits bone resorption are administered as a single composition, the molar ratio of IGF/IGFBP complex to inhibitor of bone resorption varies considerably depending on the type of bone resorption inhibitor and the formulation of the IGF/IGFBP complex. The ratio for most compounds is between about 100:1 to 1:100. Furthermore, if administered as a single composition, the IGF/IGFBP complex and the inhibitor of bone resorption may be administered as separate molecules in the composition, or the respective molecules may be conjugated or fused according to techniques well known in the art.

The precise dosage necessarily varies with the age, size, sex and condition of the subject, the nature and severity of the disorder to be treated, and the like. Thus, a precise effective amount cannot be specified in advance and must be determined by the care giver. However, appropriate amounts have been and can be determined by routine experimentation with animal models, as described below.

In general terms, an effective dose of IGF/IGFBP complex for systemic treatment will range from about 1 μg to about 10 mg IGF/kg of body weight. An effective dose for an inhibitor of bone resorption depends upon the particular inhibitor selected for administration. For example, an effective dose of estrogen is about 0.25 to 1.5 mg/day. An effective dose for bisphosphonates varies but is generally between about 0.05 μg/kg to about 15 mg/kg of body weight. An effective dose for calcitonin is about 0.05 IU (International Units or Medical Research Council Units)/kg to about 2.5 IU/kg of body weight.

Effective doses for local administration range from about 0.01 μg to 1 mg of IGF/IGFBP complex.

The methods and compositions of the invention are useful for treating bone fractures, defects, and disorders which result in weakened bones. Among these disorders are bone marrow dyscrasias such as plasma cell dyscrasias, leukemia, lymphomas, systemic mastocytosis, anemias, lipidoses and mucopolysaccharidoses; connective tissue disorders such as osteogenesis imperfecta, Ehlers-Danlos syndrome, Marfans syndrome, cutis laxa, homocystinuria, Menkes's syndrome and scurvy; osteoporosis related to such drugs as corticosteroids, heparin, oral anticoagulants, anticonvulsants, methotrexate,. thyroid hormone, lithium and gonadotrophin-releasing analogs; pregnancy; lactation; chronic hypophosphatemia; hyperphosphatasia; insulin-dependent diabetes mellitus; anorexia nervosa; Paget's disease of bone; juvenile osteoporosis; cadmium poisoning; periodontal disease; and osteoarthritis. In addition, methods and compositions of the present invention are useful in treating weakened bones resulting from disuse of the musculoskeletal system, such as occurs as a consequence of prolonged bed rest or exposure to decreased gravitational fields.

In accordance with one method of use, the IGF/IGFBP complex may be administered locally to a specific area in need of bone growth or repair, with either the concomitant administration of the inhibitor of bone resorption at the site, or the administration of the inhibitor of bone resorption in a separate vehicle. Thus, the IGF/IGFBP complex and/or inhibitor of bone resorption may be implanted directly at the site to be treated, for example, by injection or surgical implantation in a sustained-release carrier. suitable carriers include hydrogels, controlled- or sustained-release devices (e.g., an Alzet® minipump), polylactic acid, and collagen matrices. Presently preferred carriers are formulations of atelopeptide collagen containing particulate calcium phosphate mineral components, such as combinations of homologous or xenographic fibrillar atelopeptide collagen (for example Zyderm® Collagen Implant, available from Collagen Corporation, Palo Alto, Calif.) with hydroxyapatite-tricalcium phosphate (HA-TCP, available from Zimmer, Inc., Warsaw, Ind.). It is presently preferred to administer implant compositions containing an IGF/IGFBP complex and/or an inhibitor of bone resorption in a collagen/mineral mixture implant.

IGF/IGFBP complex and/or an inhibitor of bone resorption, delivered in sustained-release vehicles is also particularly useful for improving implant fixation, for example, for improving ingrowth of new bone into a metal prosthesis in joint reconstruction and dental or orthopedic implants. Alternatively, the IGF/IGFBP complex may be delivered in the implant, with the inhibitor delivered in a separate vehicle, and vice versa.

Dental and orthopedic implants can be coated with the IGF/IGFBP complex in combination with an inhibitor of bone resorption to enhance attachment of the implant device to the bone. Alternatively, the IGF/IGFBP complex can be used to coat the implant, and the inhibitor of bone resorption can be administered concomitantly or sequentially in a separate vehicle, and vice versa.

In general, implant devices may be coated with the IGF/IGFBP complex and/or an inhibitor of bone resorption as follows. The IGF/IGFBP complex (and the inhibitor of bone resorption, if desired) is dissolved at a concentration in the range of 0.01 mg/ml to 200 mg/ml in phosphate-buffered saline (PBS) containing 2 mg/ml serum albumin. The porous end of an implant is dipped in the solution and is air dried (or lyophilized) or implanted immediately into the bony site. The viscosity of the coating solution is increased, if desired, by adding hyaluronate at a final concentration of 0.1 mg/ml to 100 mg/ml or by adding other pharmaceutically acceptable excipients. Alternatively, the solution containing the IGF/IGFBP complex (and the inhibitor of bone resorption, if desired) is mixed with collagen gel or human collagen (e.g. Zyderm® Collagen Implant, Collagen Corp., Palo Alto, Calif.) to a final collagen concentration of 2 mg/ml to 100 mg/ml to form a paste or gel, which is then used to coat the porous end of the implant device. The coated implant device is placed into the bony site immediately or is air dried and rehydrated with PBS prior to implanting, with the objective of maximizing new bone formation into the implant while minimizing the ingrowth of soft tissue into the implant site.

C. EXAMPLES

The following examples are put forth so as to provide those of ordinary skill in the art with a complete disclosure and description of how to extract, isolate, formulate and use the compositions and methods of the invention and are not intended to limit the scope of what the inventors regard as their invention. Efforts have been made to insure accuracy with respect to numbers used (e.g., amounts, times, temperature, etc.), but some experimental error and deviations should be accounted for. Unless indicated otherwise, parts are parts by weight, temperature is in degrees centigrade, pressure is at or near atmospheric, and other parameters are conventional and in accordance with those normally accepted by those skilled in the art.

Example 1

This example shows the use of free IGF-I and the IGF-I/IGFBP-3 complex in female rats with ovariectomy-induced osteoporosis. In this experiment, rats were treated with human recombinant IGF-I and IGFBP-3. The rhIGF-I (Ciba-Geigy) was synthesized in yeast and provided in sterile water and stored at −70° C. The rhIGFBP-3 was made according to the procedure described in Example 4 (Celtrix Pharmaceuticals, Inc., Santa Clara, Calif.) and was dissolved in phosphate-buffered saline and stored at −70° C. until use. Prior to administration, these solutions were thawed, and sufficient amounts of IGF-I and IGFBP-3 were mixed to provide equimolar amounts of the two proteins. This experiment demonstrates the ability of the IGF-I/IGFBP-3 complex to increase trabecular bone mass and other parameters in ovariectomized rats.

In this example, young female rats of 90–100 g body weight were ovariectomized by the dorsal route and were divided into six groups of eight rats each. An additional group consisted of eight intact, age-matched sham operated control rats. Six weeks after ovariectomy, rats were treated with vehicle or with one of the following combinations of IGF-I and IGFBP-3 or IGF alone, as indicated. In these experiments, the amounts of IGF and IGFBP used were calculated to provide a 1:1 molar ratio of IGF:IGFBP:

Group 1: Sham Operated Controls; Vehicle

Group 2: Ovariectomized Controls; Vehicle

Group 3: Ovariectomized; 2.5 mg/kg IGF-I complexed to IGFBP-3 (9.5 mg/kg)

Group 4: Ovariectomized; 0.25 mg/kg IGF-I complexed to IGFBP-3 (0.95 mg/kg)

Group 5: Ovariectomized; 0.025 mg/kg IGF-I complexed to 0.095 mg/kg IGFBP-3

Group 6: Ovariectomized; 2.5 mg/kg IGF-I

Group 7: Ovariectomized; 0.25 mg/kg IGF-I

The complex was formed by mixing equimolar amounts of IGFBP-3 (dissolved in phosphate buffered saline (PBS), pH 6.0) and IGF-I (dissolved in 10 mm sodium acetate, pH 5.5) in the minimum volume feasible, and incubating the mixture overnight at 4° C. The complex was then diluted with PBS, pH 6.0, containing 0.1% rat serum albumin. The solutions were divided into aliquots containing the amount of material needed for one day, and stored at −70° C. until needed. The controls received the dilution buffer.

The rats were treated for 22 days. The test substances were administered six times per week by one daily subcutaneous injection. One day before treatment was started and on the 17th day of treatment, 20 mg/kg of calcein was given by intraperitoneal injection. Calcein and tetracycline are markers for bone mineralization and are used to estimate the amount of bone formation between administrations. Similarly, on the tenth day 20 mg/kg of demeclocycline was administered. On day 23, 24 hours after the last injection, the rats were killed by anesthesia with carbon dioxide.

Body weights were recorded throughout the experiment. At autopsy, 0.1 ml of blood was taken for the determination of blood glucose. Serum was prepared from the rest of the blood, and total serum IGF-I levels were determined by radioimmunoassay (RIA). Gastrocnemius muscle, periuterine fat and uterus were removed, dissected free of connective tissue, and weighed.

The amount of trabecular and cortical bone was determined according to Gunness-Hey ((1984) *Metab. Bone Dis. & Rel. Res.* 5:177–81), incorporated herein by reference. Briefly, the femurs were cut in half at the mid-diaphysis using a dental saw. The proximal halves were discarded. The epiphysis of the distal half was cut off using a scalpel, and the bone was split into sagittal halves. The marrow was flushed out with water. With a dental curette, the metaphyseal trabecular bone was scraped out of both cortical shells, combined and put into 5% trichloroacetic acid (TCA). The two pieces of the remaining cortical bone were also combined and put into a separate tube with 5% TCA. After this preparation stood 16 hours at room temperature, the TCA extract was used for the determination of calcium by atomic absorption spectroscopy. The remaining demineralized matrix was washed successively with ethanol and methylene chloride, and dried under vacuum. After determination of the dry weight, the matrix was hydrolyzed with 6 M HCl at 120° C. for 5 hours. In the hydrolysate hydroxyproline was determined by a standard colorimetric assay (Jamall et al. (1981) *Analyt. Biochem.* 112:70–75).

The results of this experiment are detailed in Tables 1 and 2 and summarized below.

When ovariectomized ("Ovx" in the tables) control rats were compared to sham operated control animals, no significant differences were observed in cortical bone weight or hydroxyproline (Table 2). However, cortical bone calcium was significantly increased in ovariectomized rats (7%). This increase may be due to increased longitudinal bone growth and increase in organ size. In the ovariectomized rats, trabecular bone weight, calcium and hydroxyproline were reduced by 65% (Table 1).

In ovariectomized rats treated with IGF-I alone, both doses (2.5 mg/kg and 0.25 mg/kg) increased trabecular bone mass; however, the lower dose was more effective than the higher dose. The lower dose increased various parameters 79%–118%; whereas, the higher dose increased various parameters by 57%–67%. There were marginal changes in other parameters.

Ovariectomized rats treated with IGF-I/IGFBP-3 complex showed an increase in various trabecular bone parameters (Table 1). Significant increases in trabecular calcium, dry weight, and hydroxyproline were observed at an IGF-I/IGFBP-3 dose of 12 mg/kg (2.5 mg/kg IGF-I and 9.5 mg/kg IGFBP-3). Cortical bone matrix dry weight was also increased significantly by treatment with 12 mg/kg IGF-I/IGFBP-3 complex (Table 2).

TABLE 1

| Treatment Groups | Group 1 (Sham Operated) | Group 2 (Ovx Control) | Group 3 | Group 4 | Group 5 | Group 6 | Group 7 |
|---|---|---|---|---|---|---|---|
| IGF-I (mg/kg) | — | — | 2.5 | 0.25 | 0.025 | 2.5 | 0.25 |
| IGFBP-3 (mg/kg) | — | — | 9.5 | 0.95 | 0.095 | — | — |

TABLE 1-continued

| Treatment Groups | Group 1 (Sham Operated) | Group 2 (Ovx Control) | Group 3 | Group 4 | Group 5 | Group 6 | Group 7 |
|---|---|---|---|---|---|---|---|
| Trabecular Bone[1] | | | | | | | |
| Calcium (mg) | 4.0 ± 0.4 | 1.4 ± 0.1 | 2.7 ± 0.2 | 1.8 ± 0.2 | 1.6 ± 0.1 | 2.2 ± 0.2 | 2.5 ± 0.2 |
| (%) | (+186)* | — | (+93) | (+29) | (+14) | (+57)* | (+79)* |
| Dry Weight (mg) | 2.9 ± 0.4 | 1.1 ± 0.1 | 2.1 ± 0.2 | 1.7 ± 0.2 | 1.6 ± 0.3 | 1.8 ± 0.1 | 2.4 ± 0.2 |
| (%) | (+164) | — | (+91) | (+55) | (+45) | (+64)* | (+118)* |
| Hydroxyproline | | | | | | | |
| (mg) | 269 ± 35 | 94 ± 11 | 221 ± 20 | 122 ± 20 | 157 ± 30 | 157 ± 30 | 169 ± 16 |
| (%) | (+186)* | — | (+135)* | (+30) | (+67) | (+67) | (+80)* |

[1]% are compared to ovariectomized, vehicle treated control values (Group 2)
*p < 0.05 compared to Ovx control

TABLE 2

| Treatment Groups | Group 1 (Sham Operated) | Group 2 (Ovx Control) | Group 3 | Group 4 | Group 5 | Group 6 | Group 7 |
|---|---|---|---|---|---|---|---|
| IGF-I (mg/kg) | — | — | 2.5 | 0.25 | 0.025 | 2.5 | 0.25 |
| IGFBP-3 (mg/kg) | — | — | 9.5 | 0.95 | 0.095 | — | — |
| Cortical Bone[1] | | | | | | | |
| Calcium (mg) | 24.6 ± 0.5 | 26.5 ± 0.7 | 26.1 ± 0.9 | 26.7 ± 0.7 | 23.2 ± 0.5 | 24.0 ± 0.6 | 23.5 ± 0.6 |
| (%) | (−7)* | — | (−2) | (+1) | (−12)* | (−9)* | (−11)* |
| Dry Weight (mg) | 52.8 ± 3.4 | 56.8 ± 2.7 | 64.7 ± 2.7 | 56.8 ± 3.2 | 59.1 ± 2.0 | 6.81 ± 3.6 | 55.1 ± 0.2 |
| (%) | (−7) | — | (+14)* | (±0) | (+4) | (+20)* | (−3) |
| Hydroxyproline | | | | | | | |
| (mg) | 2679 ± 177 | 2925 ± 143 | 3144 ± 146 | 2978 ± 157 | 3050 ± 1.07 | 3331 ± 102 | 3141 ± 194 |
| (%) | (−8) | — | (+7) | (+2) | (+4) | (+14)* | (+7) |

[1]% are compared to ovariectomized, vehicle treated control values (Group 2)
*p < 0.05 compared to Ovx control Example 2

Thirteen week old female Sprague Dawley rats (Charles River Associates) were housed for approximately three weeks before undergoing either ovariectomy (OVX) or sham operation (Sham). All OVXs were successful as determined by uterine weights measured at sacrifice. Eight weeks after surgery (designated day 0) the rats underwent a Dual Energy X-ray Absorptometry (DEXA) spine scan for baseline measurements of bone mineral density of vertebrae L3 through L6 (BMD) and were assigned into groups (see below). Attempts were made to exclude the "outliers" and have similar mean spine BMD values and body weights among the various groups.

The rhIGF-I/IGFBP-3 was prepared by mixing equimolar quantities of rhIGF-I and rhIGFBP-3. The vehicle employed for both rhIGF-I and rhIGF-I/IGFBP-3 was phosphate buffered saline (PBS), pH. 6.0.

Treatments (by daily subcutaneous injection) began the day after the baseline DEXA spine measurements (day 1) and continued for 56 days. Two additional "pretreatment" groups of rats (OVX and Sham) were sacrificed on day 0 to provide baseline data.

The rats were divided into seven groups according to the experimental paradigm illustrated in FIG. 1:

(1) Sham rats treated with saline ("Sham control"; n=9).
(2) OVX rats treated with saline ("OVX control"; n=11).
(3) OVX rats treated with 0.9 mg/kg/day of rhIGF-I (n=7).
(4) OVX rats treated with 2.6 mg/kg/day of rhIGF-I (n=7).
(5) OVX rats treated with 0.9 mg/kg/day of rhIGF-I in equimolar ratio with IGFBP-3 (n=8).
(6) OVX rats treated with 2.6 mg/kg/day of rhIGF-I in equimolar ratio with IGFBP-3 (n=8).
(7) OVX rats treated with 7.5 mq/kg/day of rhIGF-I in equimolar ratio with IGFBP-3 (n=8).

a. Serum Measurements

On day 22 food was withdrawn from the rats at about 7 a.m. and 150 µl of blood was obtained from the tail of each rat under isoflurane anesthesia between 10 a.m. and noon. Immediately after the blood was collected, each rat received its normal daily treatment injection, and a second blood sample was obtained exactly two hours after the injection. Food was returned to the rats only after this second bleeding. Plasma glucose levels were measured by a standard colorimetric assay involving the oxidation of O-dianisidine by the peroxide produced from glucose as a result of treatment with glucose oxidase according to standard procedures well known in the art. (Table 3)

During the seventh week of the study, blood was again obtained from the tail during the normal DEXA scan. These samples were analyzed for glycosylated hemoglobin levels using an affinity chromatographic procedure, specifically the "GLYCO-TEK" assay kit (Helena Laboratories, Beaumont, Tex.) with the eluted hemoglobins detected by their absorbances at 405 nm.

Serum obtained at sacrifice was analyzed for levels of total IGF-I, rhIGF-I and rhIGFBP-3. Serum IGF-I levels were determined by two separate assays. Each assay was performed once on the entire set of samples.

First, a Nichols Institute RIA procedure was employed to quantitate the combined concentrations of endogenous rat IGF-I and the injected rhIGF-I. Samples of 80 µl were extracted with 900 µl of 87.5% 2N HCl/12.5% ethanol, centrifuged, and then 200 µl of the supernatant was neutralized with 100 µl of 855 mM Tris buffer pH 11.0. This neutralized extract was kept at −20° C. for one hour, centrifuged, and then diluted 31-fold with phosphate buffered saline (PBS) prior to analyzing 50 µl by RIA. A preliminary assay indicated that serum obtained from hypophysectomized rats (n=6) gave values below the limit of detection (66 ng/ml) and the assay gave a linear response when the volume of serum was varied from 10 to 100 µl.

The second assay quantitated the serum levels of rhIGF-I by immunoradiometric assay (IRMA), according to protocols provided by the manufacturer, with a sample size of 10 µl. A pooled rat serum sample containing 555 ng/ml IGF-I by the Nichols Institute RIA procedure gave values below the limit of detection (50 ng/ml) of this assay. In addition, serum levels of rhIGFBP-3 on 10 µl. samples were determined by RIA. The assay kits and procedures for both rhIGF-I and rhIGFBP-3 were obtained from Diagnostic Systems Laboratories (Webster, Tex.).

Serum IGF-I and IGFBP-3 levels and blood glycosylated hemoglobin values are shown in Table 4.

TABLE 3

Fasting Plasma Glucose (mg/dl)
(Day 22 of Study)

| Group | Treatment | Time = 0 hours Glucose | SEM | Time = 2 hours Glucose | SEM | Student's P Value |
|---|---|---|---|---|---|---|
| 1 | Sham | 191 | 6 | 162 | 6 | 0.003 |
| 2 | OVX-Saline | 183 | 8 | 197 | 4 | 0.120 |
| 3 | 0.9 mg/kg IGF-I | 179 | 8 | 146 | 24 | 0.223 |
| 4 | 2.6 mg/kg IGF-I | 163 | 6 | 73 | 11 | 0.001 |
| 5 | 0.9 mg/kg IGF-I + IGFBP-3 | 175 | 7 | 195 | 9 | 0.093 |
| 6 | 2.6 mg/kg IGF-I + IGFBP-3 | 192 | 6 | 204 | 10 | 0.349 |
| 7 | 7.5 mg/kg IGF-I + IGFBP-3 | 174 | 6 | 161 | 14 | 0.432 |

TABLE 4

Serum IGF-I and IGFBP-3 Levels
and Blood Glycosylated Hemoblobin Values

| Group | Treatment | Total IGF-I (ng/ml) | rhIGF-I (ng/ml) | rhIGFBP-3 (ng/ml) | Glycosylated Hemoglobin (%) |
|---|---|---|---|---|---|
| 1 | Sham-operated + Saline | not measured | not measured | not measured | 6.7 ± 0.3 (9) |
| 2 | OVX-Saline | 487 ± 33 (9) | <50 (8) | <250 (8) | 7.2 ± 0.2 (11) |
| 3 | 0.9 mg/kg rhIGF-I | 619 ± 73 (5) | 204 ± 56 (5) | <250 (5) | 7.3 ± 0.3 (7) |
| 4 | 2.6 mg/kg rhIGF-I | 633 ± 75 (7) | 329 ± 61 (7) | <250 (7) | 7.3 ± 0.3 (7) |
| 5 | 0.9 mg/kg rhIGF-I/IGFBP-3 | 1026 ± 162 (6) | 1141 ± 294 (6) | 2.441 ± 775 (6) | 7.3 ± 0.4 (8) |
| 6 | 2.6 mg/kg rhIGF-I/IGFBP-3 | 988 ± 63 (7) | 1391 ± 10 (7) | 2372 ± 525 (7) | 7.3 ± 0.4 (8) |
| 7 | 7.5 mg/kg rhIGF-I/IGFBP-3 | 1783 ± 273 (8) | 2103 ± 123 (8) | 8217 ± 2247 (8) | 7.3 ± 0.4 (8) |
| | ANOVA P Value (Dose) | <0.001 | — | — | 0.83 |
| | ANOVA P Value (Treatment) | 0.014 | — | — | 0.69 |

Data are presented as means ± SEM for the number of values indicated in parentheses. A two-factor ANOVA was performed to determine the effects of dose (rhIGF-I and rhIGF-I/IGFBP-3 groups) and treatment (rhIGF-I versus rhIGF-I/IGFBP-3 groups.)

TABLE 4A

| | | Spine BMD (mg/cm2) | | | | | | | | | | Change | |
|---|---|---|---|---|---|---|---|---|---|---|---|---|---|
| | | Day 0 | | Day 14 | | Day 28 | | Day 42 | | Day 56 | | Days 0–56 | |
| Group | Treatment | BMD | SEM | BMD | SEM | BMD | SEM | BMD | SEM | BMD | SEM | BMD | SEM |
| A | Pretreatment Sham | 237 | 4 | ND | | ND | | ND | | ND | | ND | |
| B | Pretreatment OVX | 215 | 4 | ND | | ND | | ND | | ND | | ND | |
| 1 | Sham-Saline | 239 | 5 | 242 | 6 | 243 | 3 | 243 | 6 | 241 | 5 | 3 | 5 |
| 2 | OVX-Saline | 216 | 2 | 212 | 3 | 212 | 3 | 213 | 3 | 208 | 4 | −8 | 3 |
| 3 | 0.9 mg/kg IGF-I | 211 | 4 | 204 | 5 | 201 | 2 | 199 | 4 | 199 | 5 | −12 | 2 |
| 4 | 2.6 mg/kg IGF-I | 214 | 3 | 201 | 4 | 206 | 3 | 202 | 5 | 201 | 5 | −12 | 7 |
| 5 | 0.9 mg/kg IGF-I + IGFBP-3 | 213 | 4 | 210 | 5 | 211 | 4 | 212 | 4 | 211 | 4 | −2 | 4 |
| 6 | 2.6 mg/kg IGF-I + IGFBP-3 | 215 | 5 | 209 | 5 | 204 | 6 | 206 | 5 | 210 | 4 | −5 | 3 |
| 7 | 7.5 mg/kg IGF-I + IGFBP-3 | 219 | 5 | 215 | 4 | 214 | 5 | 213 | 4 | 219 | 4 | 0 | 3 | b. Bone Measurements

Bone surfaces undergoing active mineralization were labeled in all animals included in this study with the fluorescent bone marker declomycin and calcein by injecting those markers on days 9 and 2 prior to sacrifice, respectively.

The rats were sacrificed by exsanguination under ketamine/xylazine anesthesia. Numerous soft tissues were collected for histological analyses and some of these tissues were also weighed to examine organ hypertrophy. The long bones (tibia and femur), the spine and jaws were fixed or frozen for DEXA, mechanical and bone histomorphometric analyses according to the procedures detailed below.

1. DEXA Measurements.

Spine DEXA scans were performed on days 0 (described above), 14, 28, 42, and 56 (the day before sacrifice). DEXA whole-body scans (excluding the head and tail) for measurements of body composition (lean body mass and fat mass) were performed on days 7, 21, 35, and 49.

The DEXA measurements were made with a Hologic QDR-1000/W instrument according to directions provided by the manufacturer. The rats were anesthetized with a gaseous anesthetic of 2% isoflurane in oxygen during the scans and body weights were also obtained while the rats were anesthetized.

Parameters measured on the tibia and femurs during the DEXA analyses included length (mm), projected area ("global area") ($cm^2$), global bone mineral content (BMC) (mg), global bone marrow density (BMD) ($mg/cm^2$), global bone mineral apparent density (global BMAD=BMC divided by projected area to the 1.5 power) ($mg/cm^3$), metaphyseal BMD (met BMD) ($mg/cm^2$), cortical BMD ($mg/cm^2$), and epiphyseal BMD (epiph BMD) ($mg/cm^2$). The results are shown in Table 5 (tibia) and Table 6 (femur). In these tables, the numerical group designations correspond to those shown in FIG. 1. Groups A and B were taken for baseline measurements prior to treatment.

DEXA bone measurements were validated by comparing mineral content of the tibia as measured by both global tibia BMC values and ash weight. DEXA body composition measurements were validated by comparing the changes in body weight measured by both weighing on a balance and DEXA determinations of total body mass.

TABLE 5

DEXA Parameters on Excised Tibia

| Group | Treatment | Length Mean | Length SEM | Global Area Mean | Global Area SEM | Global BMC Mean | Global BMC SEM | Global BMD Mean | Global BMD SEM | Global BMAD Mean | Global BMAD SEM | Met BMD Mean | Met BMD SEM | Cortical BMD Mean | Cortical BMD SEM | Epiph BMD Mean | Epiph BMD SEM |
|---|---|---|---|---|---|---|---|---|---|---|---|---|---|---|---|---|---|
| A | Sham - Pretreatment | 39.8 | 0.4 | 1.41 | 0.02 | 323 | 7 | 229 | 3 | 193 | 2 | 241 | 3 | 216 | 3 | 287 | 6 |
| B | OVX - Pretreatment | 40.4 | 0.1 | 1.39 | 0.02 | 286 | 6 | 206 | 2 | 175 | 2 | 187 | 4 | 211 | 3 | 235 | 2 |
| 1 | Sham - Saline | 40.3 | 0.4 | 1.44 | 0.04 | 310 | 9 | 221 | 2 | 184 | 2 | 217 | 6 | 209 | 3 | 276 | 5 |
| 2 | OVX - Saline | 40.7 | 0.6 | 1.46 | 0.02 | 313 | 7 | 215 | 3 | 178 | 2 | 198 | 3 | 221 | 3 | 231 | 3 |
| 3 | 0.9 mg/kg IGF-I | 40.4 | 0.4 | 1.39 | 0.04 | 284 | 12 | 205 | 4 | 174 | 2 | 192 | 5 | 210 | 6 | 217 | 6 |
| 4 | 2.6 mg/kg IGF-I | 41.7 | 0.4 | 1.48 | 0.02 | 316 | 7 | 214 | 3 | 176 | 3 | 196 | 5 | 221 | 4 | 226 | 4 |
| 5 | 0.9 mg/kg IGF-I + IGFBP-3 | 41.2 | 0.3 | 1.46 | 0.03 | 306 | 7 | 210 | 2 | 174 | 3 | 197 | 4 | 215 | 3 | 223 | 5 |
| 6 | 2.6 mg/kg IGF-I + IGFBP-3 | 40.8 | 0.5 | 1.50 | 0.04 | 332 | 10 | 223 | 3 | 182 | 3 | 200 | 4 | 227 | 2 | 237 | 4 |
| 7 | 7.5 mg/kg IGF-I + IGFBP-3 | 42.0 | 0.2 | 1.59 | 0.02 | 355 | 4 | 223 | 3 | 177 | 3 | 204 | 3 | 233 | 3 | 238 | 4 |

TABLE 6

DEXA Parameters on Excised Femurs

| Group | Treatment | Length Mean | Length SEM | Global Area Mean | Global Area SEM | Global BMC Mean | Global BMC SEM | Global BMD Mean | Global BMD SEM | Global BMAD Mean | Global BMAD SEM | Met BMD Mean | Met BMD SEM |
|---|---|---|---|---|---|---|---|---|---|---|---|---|---|
| A | Sham - Pretreatment | 36.1 | 0.3 | 1.68 | 0.02 | 419 | 10 | 250 | 3 | 193 | 2 | 226 | 4 |
| B | OVX - Pretreatment | 35.9 | 0.3 | 1.60 | 0.02 | 360 | 7 | 223 | 3 | 175 | 3 | 172 | 5 |
| 1 | Sham - Saline | 36.5 | 0.3 | 1.71 | 0.03 | 429 | 15 | 250 | 5 | 191 | 2 | 212 | 5 |
| 2 | OVX- Saline | 36.9 | 0.3 | 1.75 | 0.03 | 401 | 10 | 229 | 2 | 173 | 1 | 177 | 3 |
| 3 | 0.9 mg/kg IGF-I | 36.2 | 0.4 | 1.69 | 0.04 | 370 | 15 | 218 | 4 | 168 | 2 | 167 | 4 |
| 4 | 2.6 mg/kg IGF-I | 37.6 | 0.4 | 1.78 | 0.02 | 411 | 10 | 231 | 3 | 173 | 1 | 173 | 3 |
| 5 | 0.9 mg/kg IGF-I + IGFBP-3 | 37.0 | 0.3 | 1.76 | 0.03 | 394 | 10 | 224 | 4 | 169 | 3 | 169 | 5 |
| 6 | 2.6 mg/kg IGF-I + IGFBP-3 | 37.4 | 0.3 | 1.80 | 0.04 | 424 | 13 | 235 | 4 | 175 | 2 | 174 | 4 |
| 7 | 7.5 mg/kg IGF-1 + IGFBP-3 | 37.9 | 0.2 | 1.86 | 0.02 | 451 | 7 | 243 | 2 | 178 | 2 | 174 | 3 |

2. Bone Histomorphometry and Structure

Right femurs, tibias and lumbar vertebral bodies (Lvb; $L_4$–$L_5$) were collected at necropsy, cleaned of soft tissues, fixed in 70% ethanol for 48 h, dehydrated through upgraded ethanols, and embedded undecalcified in methyl methacrylate. Longitudinal sections of distal femoral epiphyses, metaphyses, Lvb, and cross-sections of the mid femoral neck and the distal tibial diaphyses proximal to the tibiofibular junction were cut with a Reichert-Jung supercut microtome (Reichert-Jung, Heidelberg, Germany) to 15 μm in thickness. Three consecutive sections were left unstained for dynamic histomomorphometric analyses and the other three sections were stained by the von Kossa method for mineral, counterstained with toluidine blue, and analyzed for static histomorphometic parameters. The 100 μm thick cross-sections from femoral midshaft and mid-neck region were cut with a precision low-speed bone saw (Isomet, Buehler, Lake Bluff, Ill.), glued to plastic slides, ground and polished to ≈40 μm in thickness (Ecomet 3, Buehler, Lake Bluff, Ill.) and analyzed for bone dynamic parameters. The same set of slides were used for static bone histomorphdmetry after being stained with the von Kossa method and covered with cover slips. Bone dynamic measurements were performed under UV light and 20-fold magnification by using a semi-automated software program called "Stereology" (KSS Computer Engineers, Magna, Utah) described earlier by Miller et al. (1989) *Bone* 7:283–287. Static bone analyses were performed with an automated television microscope image analysis system and analyzed using "Image Analysis" software (KSS Computer Engineers, Magna, Utah).

For the femoral neck only, internal structure of trabecular bone, interconnectivity, and connectivity between endocortical surface and trabecular network, the "Nodal" and "Star volume" analyses were performed as described by Miller and Wronski (1993) *Anat. Record* 236:433–441 and Bagi and Miller (1954) *Anat. Record* 239:1–12. The marrow star volume is a direct measure of trabecular separation, while the nodal analysis describes the number of nodes and struts, type of struts, and number of inter-trabecular connectivity. Connections between endocortical surface and trabecular network are important determinants of bone strength linking cortical and cancellous bone into one anatomico-functional unit. The total number of endocortico-trabecular connections was counted and the percentages of free ending trabeculae versus those connected with other trabeculae and/or the endocortical surface were calculated. All measurements and derived parameters describing bone dynamic and structure were performed as recommended by ASBMR Histomorphometric Committee (Parfitt et al. (1987) *J. Bone Min. Res.* 2:595–610.

3. Bone Failure Strength and Internal Cortical Bone Structure

Left femurs were cleaned of soft tissue and were used in DEXA measurements of bone mineral density (BMD) and bone, mineral content (BMC). To test the biomechanical properties of the cortical bone, the proximal and distal ends of each femur were secured in test fixtures, designed to allow freedom of motion parallel to the long axis of the bone. The fixtures were mounted in an MTS 858 Bionix System (MTS System Corp., Minneapolis, Minn.) and torque was measured with an externally conditioned miniature torque transducer (range 0–50 in-lbs; Model QWFK-8M/1941, Sensotec, Columbus, Ohio) as described earlier (van der Meulen, M. C. H., "Bone Strength in Young, Suspended Rats, Stanford University Thesis, 1993). (Mechanical tests were performed at the Department of Mechanical Engineering, Stanford University, Stanford, Cailf.; and Rehabilitation Research and Development Center, Palo Alto, Calif.; and VA Medical Center, Palo Alto, Calif.). After mechanical testing, the same specimens were dehydrated in graded ethanols, embedded in methyl methacrylate, and cut with a low speed bone saw (Isomet, Buehler, Lake Bluff, Ill.) to ≈100 μm in thickness. The cross-sections (2–3) from the femoral proximal midshafts were glued on plastic slides, ground and polished to ≈40 μm thickness and analyzed under polarized light for cortical bone internal structure. The measurements included thickness of the inner and outer lamellar bone layer and thickness of the medially placed woven bone. Following these measurements, samples were stained by the von Kossa method, counterstained with toluidine blue and coverslipped. Static bone analyses were performed including the calculation of the second moment of inertia parameter.

4. Cellular Bone Analyses

Right tibias were fixed in 10% neutral buffered formalin for 48 h, demineralized in Cal-Rite decalcifying solution (Richland-Allan Medical, Richland, Mich.) for two weeks and processed for paraffin embedding. Three μm thick longitudinal sections through the proximal tibial metaphysis were stained with hematoxylin and eosin and Gomori's trichrome and were used for cellular bone analyses.

5. Statistical Analyses

Differences between plasma glucose values at zero and two hours in Table 3 were analyzed by Student's t-test. A two-factor analysis of variance was employed in Table 3 for comparing differences between treatment groups. Differences between the groups shown in Tables 7–16 or FIGS. 2a–b, 3, 4, 7a–d were tested for significance in a one-way analysis of variance. When the analysis of variance indicated significant differences among means, the differences were evaluated using Dunnat's t-test and Fisher's Protected Least Significant Difference method for multiple comparisons (Netter et al. (1982) "Applied Statistics," Allyn and Bacon, Boston.) Statistical significance was considered at $P<0.05$, and results were expressed as the mean ± standard error (SE).

c. Results

Analysis of data revealed site-specific alterations of cortical and cancellous bone to ovariectomy and treatment with rhIGF-I and rhIGF-I/IGFBP-3 complex. As shown in Table 3, the 2.5 mg/kg dose of rhIGF-I caused acute hypoglycemia which did not occur with any of the doses of rhIGF-I/IGFBP-3. The data presented in Table 4 indicate that no treatment had any influence on glycosylated hemoglobin values and that increasing doses of rhIGF-I and rhIGFBP-3 led to higher serum levels of total IGF-I, rhIGF-I and rhIGFBP-3. Combining rhIGF-I with rhIGFBP-3 resulted in higher serum values of these agents than observed in rats treated with only rhIGF-I.

Spine BMD data throughout the study along with means of the individual changes are presented in Table 4A. As expected, ovariectomy led to a decline in spine BMD which was prevented by the 7.5 mg/kg dose of rhIGF-I/IGFBP-3. Some protection was observed with the two lower doses of rhIGF-I/IGFBP-3 but not with the two doses of rhIGF-I. The DEXA data obtained on excised tibia (Table 5) and femurs (Table 6) show dose-related increases in global BMC and global BMD for both rhIGF-I and rhIGF-I/IGFBP-3.

1. Cortical Bone

Figure 4A:
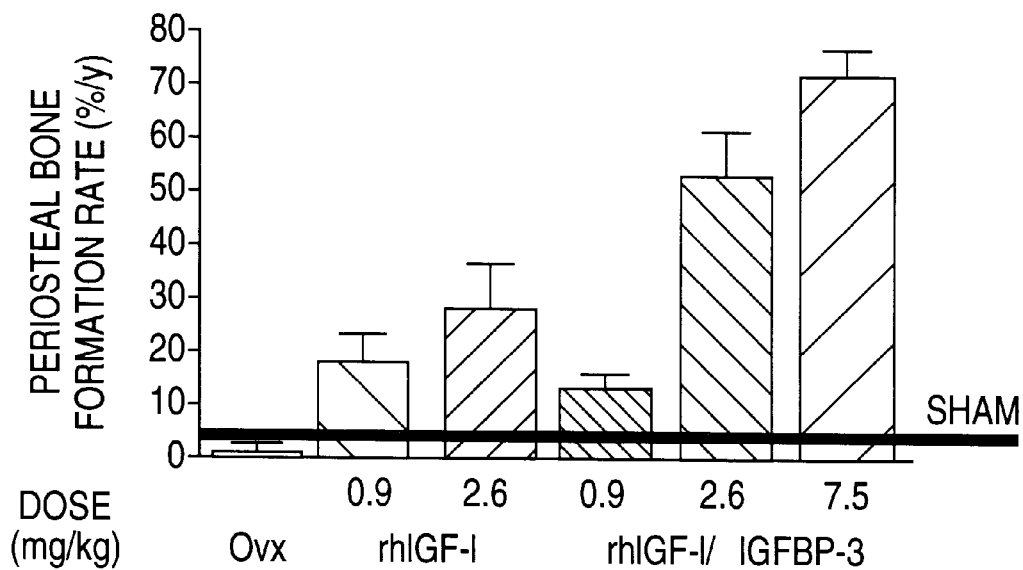
FIGS. 4A and 4B show bar graphs of tibial periosteal bone formation rate (4A) and tibial endocortical resorption (4B) of ovariectomized (OVX) animals treated for 8 weeks with rhIGF-I or rhIGF-I/IGFBP-3 complex at the doses of IGF-I indicated, compared to no treatment (solid bars) and sham operated controls (solid line)
Figure 4B:
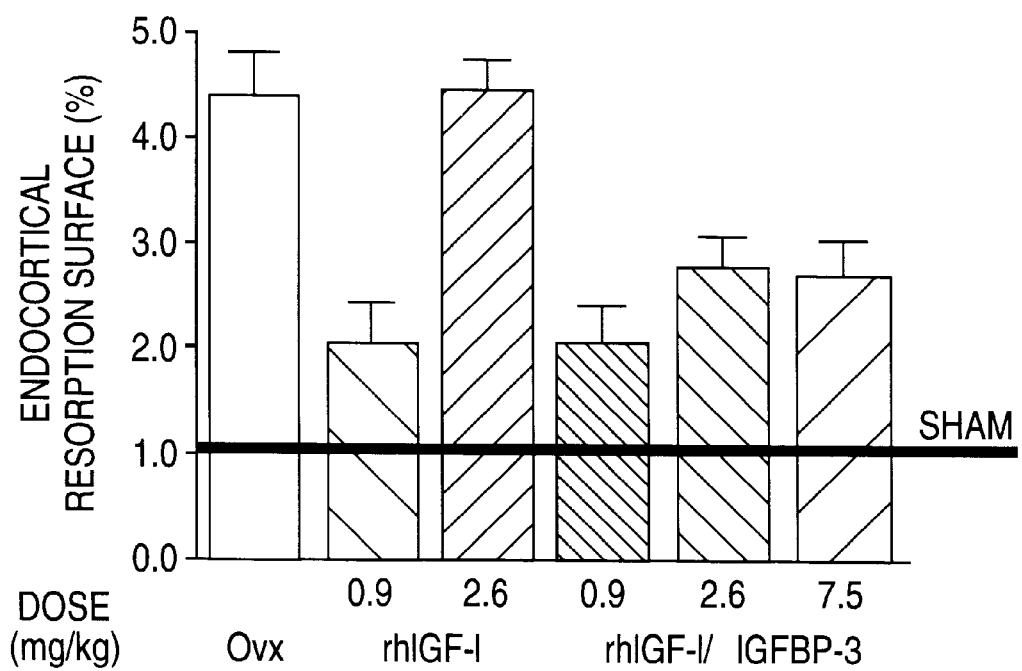
Figure 5A:
FIGS. 5A–5CC show matching UV micrographs (5A–5C, 3× magnification; 5CC, 12× magnification of periosteal envelope region shown in 5C) of ground 40 $\mu$m thick tibial cross-sections from sham (5A), OVX (5B), and OVX rats treated with 7.5 mg/kg rhIGF-I complexed with rhIGFBP-3 (5C, 5CC) where new bone formation on the periosteal envelope is indicated by the arrows.
Figure 5B:
Figure 5C:
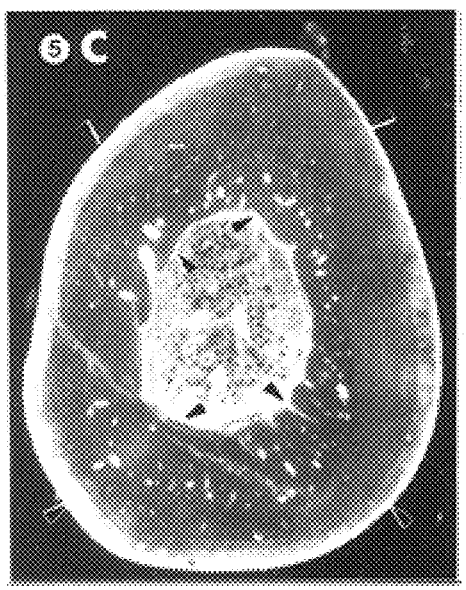
Figure 5D:
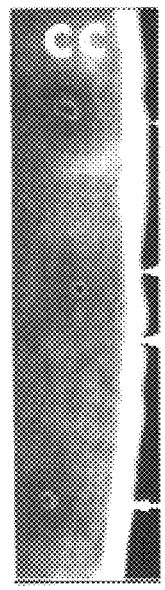
Figure 6A:
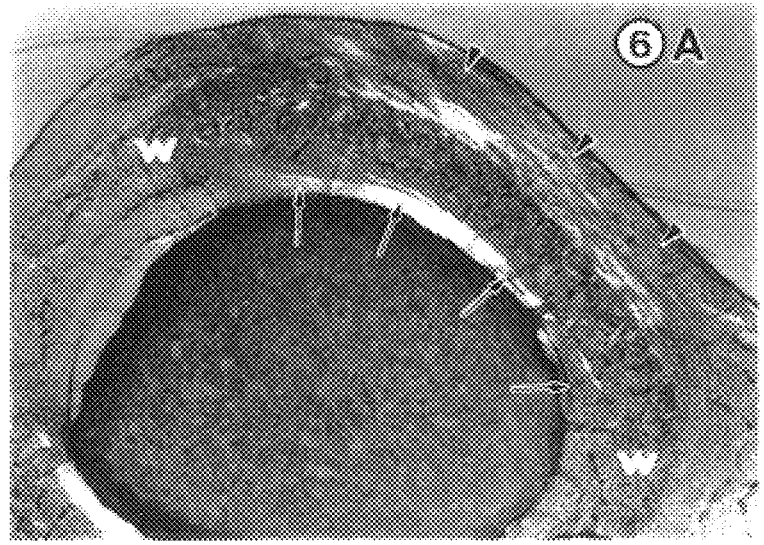
FIGS. 6A–6D show polarized light micrographs (12.5× magnification) of unstained, 40 $\mu$m thick cross sections from Sham operated animals (6A), OVX animals (6B), and from animals treated with 7.5 mg/kg rhIGF-I complexed with rhIGFBP-3 (6C, 6D), where outer lamellar layers are indicated by arrowheads and inner lamellar layers are indicated by arrows.
Figure 6B:
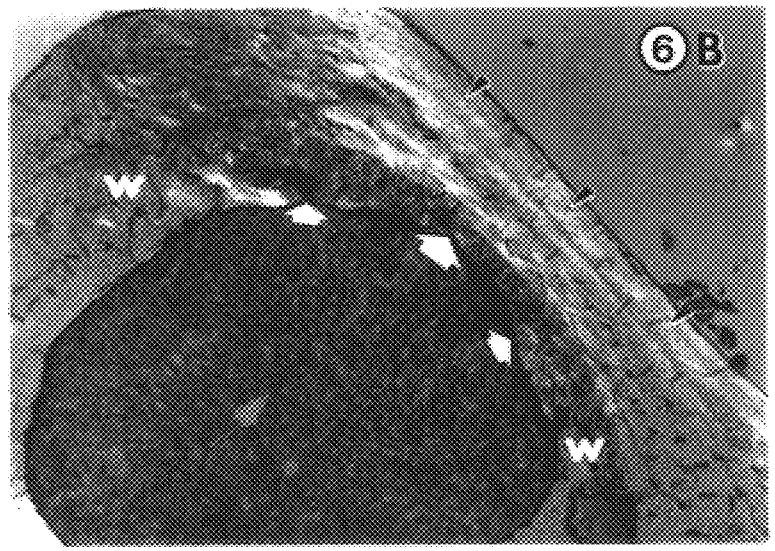
Figure 6C:
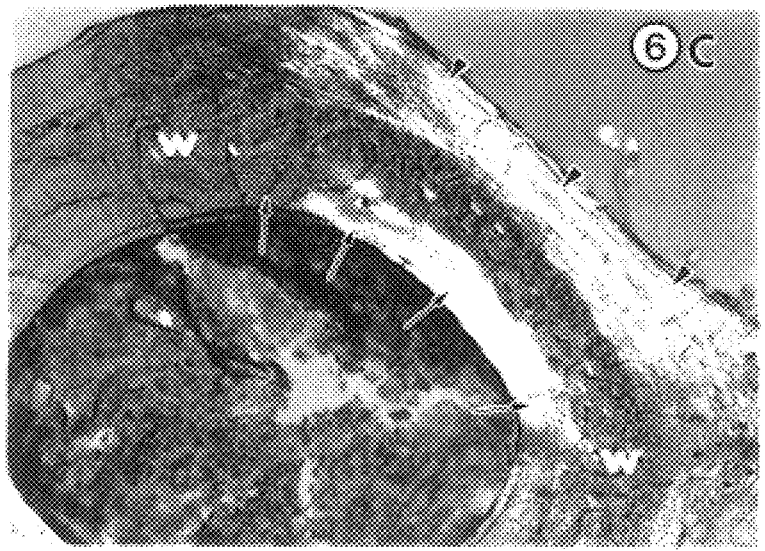
Figure 6D:
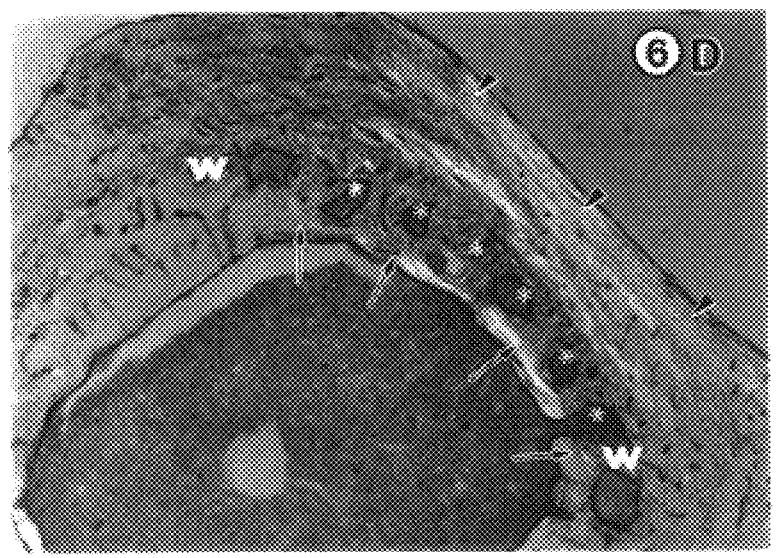

Treatment with both formulations tested caused a dose dependent increase in the body weight and in the lean body mass of treated rats (FIGS. 2A and 2B). Periosteal bone formation activity was higher in all treated groups and at all sites measured relative to Sham or OVX controls (Tables 7, 8, 9, 11). However, the group of rats treated with 7.5 mg/kg of rhIGF-I/IGFBP-3 complex exhibited the highest increase in the periosteal bone formation rate parameter (FIGS. 4A and 5C, 5CC).

Endocortical bone resorption in treated rats, which is a hallmark of cortical bone changes in estrogen deficient women and rats, were not different from values obtained for the Sham-op controls (FIG. 4B), showing significantly lower values compared to OVX rats at the femoral neck location (Table 11). Also, bone formation at the endocortical envelope was increased at both bone sites measured (femoral diaphyses, Table 8).

Internal structural analyses showed normal "lamellar" configuration of the bone formed on both cortical envelopes after rhIGF-I/IGFBP-3 treatment (Table 9; FIG. 6). Increased modeling-dependent bone formation on the periosteal and endocortical bone envelopes and moderate or decreased bone resorption on the endocortical envelope resulted in thicker cortical bone in the treated rats (Table 7, 9, 11; FIGS. 5 and 6). Increased cortical thickness and newly formed lamellar bone which is mechanically superior to woven bone resulted in the higher failure torque and polar moment of inertia parameters in rats treated with 7.5 mg/kg of rhIGF-I/IGFBP-3 complex (Table 10).

All treated animals exhibited similar increases in lbngitudinal bone growth when compared to OVX of Sham rats (FIG. 3). In general, treatment with rhIGF-I/IGFBP-3 caused cortical bone thickening by adding "lamellar" bone on both envelopes. The increase in lean body component might potentiate periosteal bone formation by increasing the muscle pull on the periosteum. Both "lamellar" structure and increased cortical thickness improved cortical bone strength after rhIGF-I/IGFBP-3 treatment.

2. Cancellous Bone

Figure 7A:
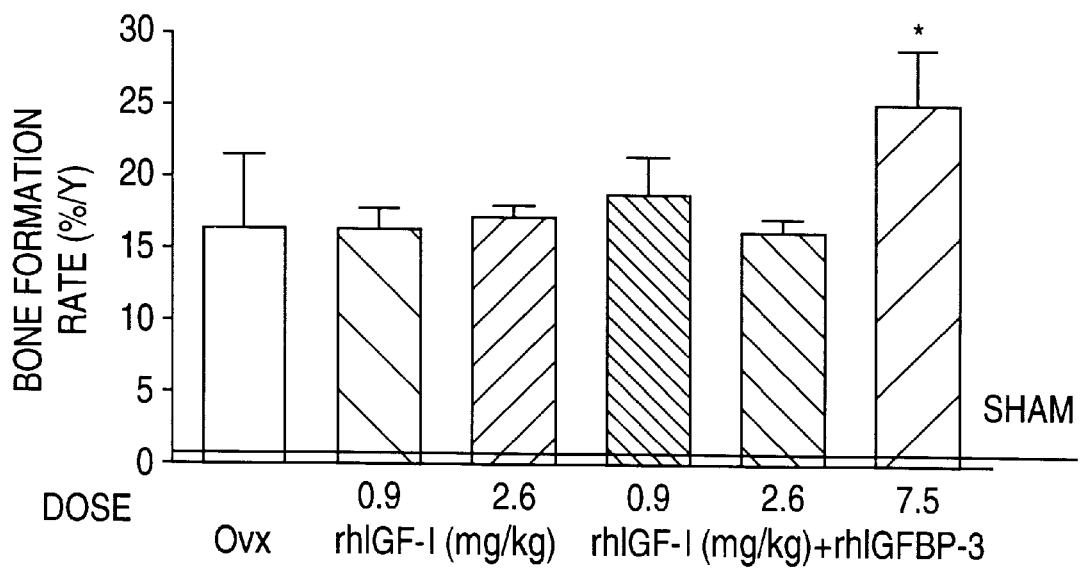
Figure 7B:
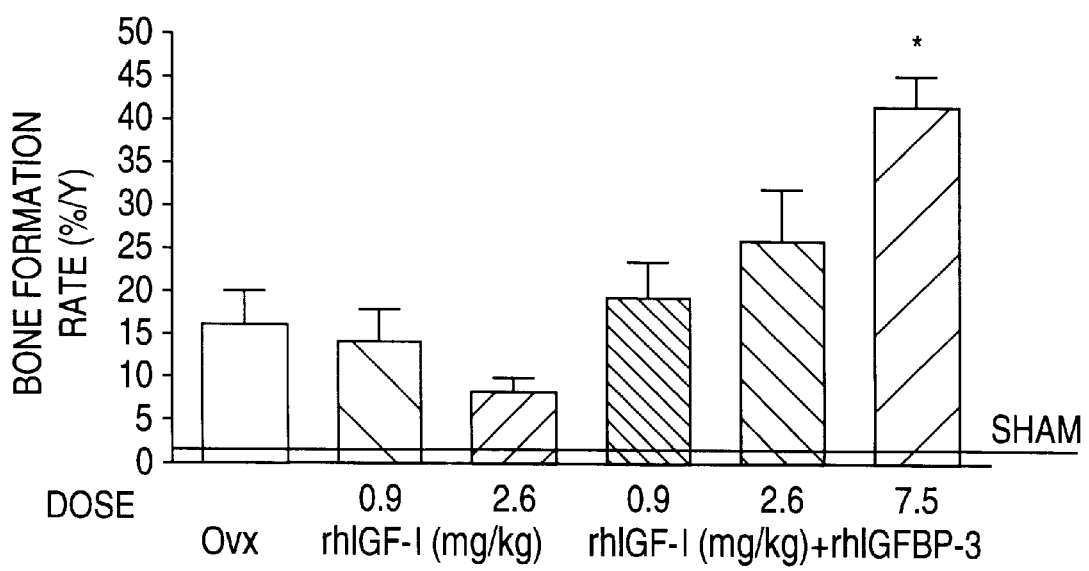
Figure 8A:
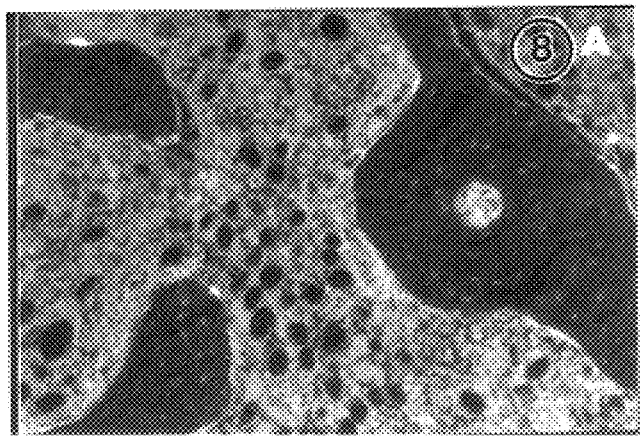
FIGS. 8A–8C show UV micrographs of cancellous trabeculae in distal femoral epiphysis from sham-operated control (8A), OVX (8B) and 7.5 ml/kg rhIGF-I/IGFBP-3 complex (8C) treated rats, where arrows indicate resorption pits and arrowheads indicate newly formed bone.
Figure 8B:
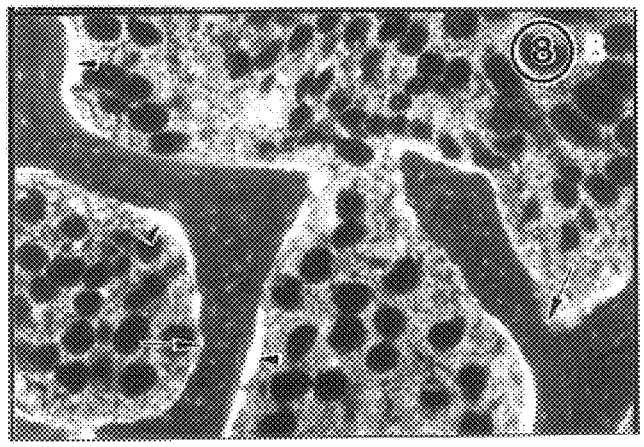
Figure 8C:
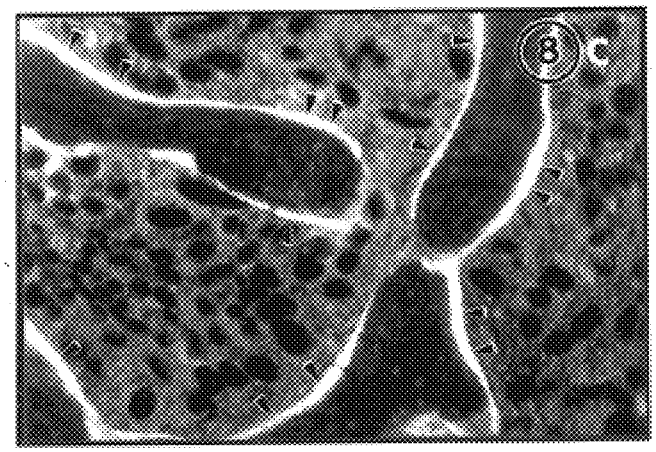

Cancellous bone dynamics and structure were examined at four different locations in the rat skeleton. Differences in different locations in the bone turnover rates and functional anatomy between the designated sites (distal femoral epiphysis, distal femoral metaphysis, femoral mid-neck, and lumbar vertebral bodies) were measured. Treatment with rhIGF-I/IGFBP-3 increased bone formation parameters at all four sites (Tables 12, 13, 14, 15; FIGS. 7 and 8). The increase in bone formation rates (volume referents; FIGS. 7A–7D) was the highest in the group treated with 7.5 mg/kg of rhIGF-I/IGFBP-3 complex. Bone resorption had similar or lower values compared to OVX rats (Tables 12–15). Such turnover activity resulted in increased trabecular thickness and preservation of the trabecular number in treated rats at all sites measured, except in the femoral metaphysis.

Figure 9A:
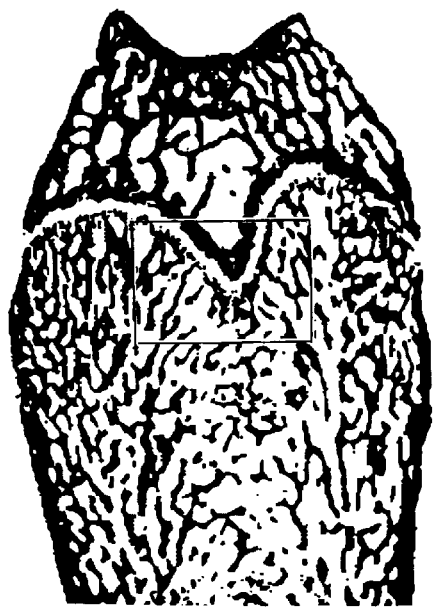
FIGS. 9A–9C show matching micrographs (3× magnification) of 4 $\mu$m section taken from distal femurs stained by the mineral-staining method of von Kossa from sham-operated controls (9A) OVX (9B) and 7.5 mg/kg rhIGF-I/IGFBP-3 complex treated rats (9C)
Figure 9B:
Figure 9C:

Primary and secondary spongiosa at the femoral metaphyseal site was highly affected by the endochondral bone elongation, particularly in the OVX rats and after treatment with rhIBF or rhIBF-I/IBFBP-3 (FIGS. 9A–9C). This bone site has the highest bone turnover rate. Ovx caused disappearance of "metabolic" trabeculae in the central metaphyseal region with no mechanical value (FIG. 9B) while treatment with rhIGF-I/IGFBP-3 complex helped the restoration (FIG. 9C).

Figure 10A:
FIGS. 10A–10C show cross-sectional images (2.5× magnification) of sections taken from femoral mid-neck region of sham-operated control (10A), OVX rats (10B) and from rats treated with 7.5 mg/kg rhIGF-I complexed with IGFBP-3 (10C)
Figure 10B:
Figure 10C:

Structural trabecular bone analyses were performed at the femoral neck location, which is the most relevant bone site for fractures in humans (Table 16; FIGS. 10A–10C). Besides having a very unique anatomy, this bone site combines cortical and cancelious bone interconnected at the endocortical surface. Cortical bone thickness, cancellous bone mass, structure, and connectivity between endocortical surface and trabecular network are all important determinants of the bone strength in the femoral neck region. The treatment with the rhIGF-I/IGFBP-3 improved trabecular bone structure and connectivity between the trabecular network and endocortical surface. In general, data presented here revealed benefits of systemically administered rhIBF-I/IBFBP-3 on the entire musculo-skeletal system in previously ovariectomized rats.

TABLE 7

Cortical bone morphometry measured at the tibio-fibularjunction in rats treated with rhIGF-I alone, or with equimolar doses of rhIGF-I/IGFBP-3 complex for eight weeks.

| Parameter | Sham | Ovx | rhIGF-I (mg/kg) | | rhIGF-I (mg/kg) + rhIGFBP-3 | | |
|---|---|---|---|---|---|---|---|
| | | | 0.9 | 2.6 | 0.9 | 2.6 | 7.5 |
| Periosteal perimeter (mm) | 8.64 ± 0.12 | 9.24 ± 0.15† | 9.19 ± 0.18† | 9.29 ± 0.27†,* | 9.21 ± 0.21† | 9.43 ± 0.17†,* | 9.55 ± 0.17†,* |
| Endocortical perimeter (mm) | 3.56 ± 0.06 | 4.03 ± 0.18† | 3.8 ± 0.15 | 4.12 ± 0.2† | 3.73 ± 0.14 | 3.69 ± 0.09[b] | 3.71 ± 0.11† |
| Organ area (mm$^2$) | 5.52 ± 0.09 | 5.69 ± 0.18† | 5.59 ± 0.27 | 5.83 ± 0.24† | 5.63 ± 0.18 | 5.78 ± 0.14* | 6.27 ± 0.16†, * |
| Marrow area (mm$^2$) | 0.95 ± 0.02 | 1.08 ± 0.05† | 0.92 ± 0.09 | 1.03 ± 0.06† | 0.67 ± 0.05†,* | 0.81 ± 0.05* | 0.93 ± 0.04* |
| Cortical area (mm$^2$) | 4.57 ± 0.07 | 4.62 ± 0.13† | 4.68 ± 0.29* | 4.8 ± 0.17†,* | 4.95 ± 0.14†,* | 4.97 ± 0.13†,* | 5.34 ± 0.14†,* |
| Percent periosteal double labeled surface (%) | 11.76 ± 4.6 | 10.33 ± 2.9† | 43.09 ± 8.4†,* | 67.27 ± 9.6†,* | 44.12 ± 3.8†,* | 73.09 ± 4.5†,* | 90.04 ± 2.2†.* |
| Periosteal new bone area ($\mu$m$^2$) | 0.004 ± 0.002 | 0.002 ± 0.001† | 0.02 ± 0.01†,* | 0.03 ± 0.01†,* | 0.02 ± 0.004†,* | 0.07 ± 0.01†,*,[b] | 0.09 ± 0.004†,* |
| Periosteal mineralized surface (%) | 12.16 ± 4.7 | 8.33 ± 3.2† | 43.52 ± 8.8†,* | 52.29 ± 9.0†,* | 44.68 ± 4.1†,* | 63.65 ± 5.5†,* | 84.26 ± 2.8†.* |
| Periosteal mineral appositional rate ($\mu$m/d) | 0.33 ± 0.17 | 0.17 ± 0.12† | 0.71 ± 0.05†,* | 1.03 ± 0.08†,* | 0.62 ± 0.04†,* | 1.42 ± 0.1†,*,[b] | 1.43 ± 0.02†,* |
| Periosteal bone formation rate ($\mu$m$^2$/$\mu$m/d) | 0.06 ± 0.03 | 0.02 ± 0.02 | 0.27 ± 0.08†,* | 0.4 ± 0.11†,* | 0.21 ± 0.04†,* | 0.77 ± 0.11†,*,[b] | 1.09 ± 0.06†,* |
| Periosteal bone formation rate (%/y) | 5.22 ± 2.18 | 1.63 ± 3.65 | 18.39 ± 14.2†,* | 28.8 ± 8.78†,* | 13.67 ± 6.8†,* | 53.7 ± 13.8†, *,[b] | 72.6 ± 12.5†,* |

Data are expressed as the mean ± SE;
†Significantly different from Sham group, P < 0.05 by Dunnett's test;
*Significantly different from Ovx group, P < 0.05 by Dunnett's test; [b]Signiflcantly different from rhIGF-I (2.6 mg/kg) group, P < 0.05 by Fisher's PLSD test.

TABLE 8

Dynamic cortical bone parameters measured at the femoraldiaphyses in control rats and rats treated with 7.5 mg/kg of rhIGF-I/IGFBP-3 complex for eight weeks.

| Parameter | Basal Sham | Basal Ovx | Sham | Ovx | IGF-I/IGFBP-3 |
|---|---|---|---|---|---|
| Periosteal mineralizing surface (%) | 50.18 ± 5.26 | 58.34 ± 3.15 | 41.38 ± 3.66[b] | 32.87 ± 4.05[a,b] | 86.45 ± 4.72[a,b,c,d] |
| Periosteal mineral appositional rate ($\mu$m/d) | 0.61 ± 0.02 | 1.03 ± 0.04[a] | 0.76 ± 0.05[a,b] | 0.83 ± 0.04[a,b] | 1.29 ± 0.07[a,b,c,d] |
| Periosteal bone formation rate ($\mu$m$^2$/$\mu$m/d) | 0.23 ± 0.03 | 0.49 ± 0.02[a] | 0.26 ± 0.03[b] | 0.2 ± 0.04[b] | 1.07 ± 0.13[a,b,c,d] |
| Periosteal bone formation rate (%/y) | 21.27 ± 2.5 | 45.85 ± 0.09[a] | 24.89 ± 1.48[b] | 21.4 ± 3.02[b] | 88.81 ± 10.3[a,b,c,d] |
| Endocortical mineralizing surface (%) | 1.02 ± 0.43 | 4.03 ± 0.69 | 1.69 ± 0.27 | 2.14 ± 0.4[c] | 17.79 ± 4.22[a,b,c,d] |
| Endocortical mineral appositional rate ($\mu$m/d) | 0.009 ± 0.01 | 0.425 ± 0.19[a] | 0.068 ± 0.06[b] | 0.052 ± 0.05[b] | 0.807 ± 0.13[a,b,c,d] |
| Endocortical bone formation rate ($\mu$m$^2$/$\mu$m/d) | 0.008 ± 0.05 | 0.023 ± 0.01 | 0.002 ± 0.001 | 0.001 ± 0.001 | 0.173 ± 0.046[a,b,c,d] |
| Endocortical bone formation rate (%/y) | 0.04 ± 0.02 | 2.16 ± 0.86 | 0.42 ± 0.42 | 0.32 ± 0.32 | 7.79 ± 2.35[a,b,c,d] |
| Endocortical resorption surface (%) | 1.01 ± 0.25 | 4.14 ± 0.8[a] | 1.79 ± 0.23[b] | 6.33 ± 0.79[a,b,c] | 2.71 ± 0.33[a,d] |

Data are expressed as the mean ± SE; Significant difference $P < 0.05$ by Fisher's PLSD test.
[a]Significantly different from Basal Sham group;
[b]Significantly different from basal Ovx group;
[c]Significantly different from Sham group;
[d]Significantly different from Oxv group.

TABLE 9

Static cortical parameters measured at the femoralmidshafts, and structural parameters measured at the postero-lateral ¼ of the cross-sectional areas in control rats and rats treated with 7.5 mg/kg of rhIGF-I/IGFBP-3 complex for eight weeks.

| Parameter | Basal Sham | Basal Ovx | Sham | Ovx | IGF-I/IGFBP-3 |
|---|---|---|---|---|---|
| Periosteal perimeter (mm) | 9.54 ± 0.09 | 9.65 ± 0.23 | 9.76 ± 0.11 | 10.51 ± 0.19[a,b,c] | 11.61 ± 0.41[a,b,c,d] |
| Endocortical perimeter (mm) | 5.4 ± 0.13 | 5.79 ± 0.18 | 5.38 ± 0.12 | 5.98 ± 0.18[a,c] | 5.69 ± 0.15 |
| Organ area (mm$^2$) | 6.02 ± 0.13 | 5.89 ± 0.22 | 6.05 ± 0.16 | 6.65 ± 0.19[a,b,c] | 7.03 ± 0.15[a,b,c] |
| Marrow area (mm$^2$) | 1.76 ± 0.05 | 2.0 ± 0.13 | 1.82 ± 0.09 | 2,18 ± 0.13[a,c] | 1.86 ± 0.09[d] |
| Cortical area (mm$^2$) | 4.26 ± 0.09 | 3.89 ± 0.1 | 4.23 ± 0.12 | 4.46 ± 0.09[b] | 5.17 ± 0.09[a,b,c,d] |
| Average cortical width ($\mu$m) | 601.4 ± 7.9 | 568.6 ± 1.5[a] | 597.5 ± 6.1[b] | 574.8 ± 3.8[a,c] | 614.8 ± 5.6[b,c,d] |
| Percent cortical area (%) | 70.7 ± 0.5 | 69.16 ± 0.77 | 69.9 ± 1.1 | 67.3 ± 1.2[a] | 73.6 ± 0.9[a,b,c,d] |
| Structural parameters: | | | | | |
| Outer lamellar layer ($\mu$m) | 277.1 ± 8.9 | 273.5 ± 8.4 | 274.5 ± 11.3 | 316.8 ± 14.6[a,b,c] | 280.3 ± 10.1[d] |
| Central woven layer ($\mu$m) | 119.8 ± 5.1 | 114.6 ± 6.0 | 120.5 ± 6.4 | 103.7 ± 14.5 | 114.2 ± 6.2 |
| Inner lamellar layer ($\mu$m) | 213.3 ± 8.1 | 145.4 ± 11.2[a] | 202.6 ± 9.2[b] | 70.4 ± 8.8[a,b,c] | 242.6 ± 13.7[a,b,c,d] |

Data are expressed as the mean ± SE; Significant difference $P < 0.05$ by Fisher's PLSD test.
[a]Significantly different from Basal Sham group;
[b]Significantly different from Basal Ovx group;
[c]Significantly different from Sham group;
[d]Significantly different from Ovx group.

TABLE 10

Femoral failure strength and general parameters in control rats and rats treated with 7.5 mg/kg of rhIGF-I/IGFBP-3 complex for eight weeks.

| Parameter | Basal Sham | Basal Ovx | Sham | Ovx | IGF-I/IGFBP-3 |
|---|---|---|---|---|---|
| Failure torque (N/mm) | 461.9 ± 526.8 | 387.0 ± 41.1[a] | 390.6 ± 31.2 | 443.6 ± 21.2[b,c] | 471.5 ± 15.3[b,c,d] |
| Torsional rigidity (Ncm$^2$/rad) | 454 ± 58 | 43.9 ± 66 | 468 ± 98 | 479 ± 93 | 468 ± 39 |
| Linear stiffness (N-m/degrees) | 43.4 ± 2.6 | 40.7 ± 2.5 | 42.6 ± 2.5 | 43.1 ± 3.9 | 44.9 ± 2.8 |
| Polar moment inertia (mm$^4$) | 6.6 ± 0.7 | 6.3 ± 0.9 | 6.5 ± 0.6 | 6.8 ± 1.3[b] | 9.3 ± 1.8[a,b,d] |
| Femoral length (mm) | 36.0 ± 0.3 | 35.8 ± 0.3 | 36.6 ± 0.4 | 36.8 ± 0.4[b] | 37.9 ± 0.2[a,b,c,d] |
| Femoral area (cm$^2$) | 1.67 ± 0.03 | 1.66 ± 0.04 | 1.73 ± 0.03 | 1.74 ± 0.04 | 1.86 ± 0.02[a,b,c,d] |
| Femoral BMC (g) | 0.41 ± 0.01 | 0.37 ± 0.01[a] | 0.44 ± 0.02[b] | 0.34 ± 0.01[c] | 0.45 ± 0.01[a,b,d] |
| Femoral BMD (g/cm$^2$) | 0.25 ± 0.003 | 0.23 ± 0.004[a] | 0.25 ± 0.01[b] | 0.23 ± 0.003[a,c] | 0.24 ± 0.002[b,d] |

Data are expressed as the mean ± SE; Significant difference $P < 0.05$ by Fisher's PLSD test.
[a]Significantly different from Basal Sham group;
[b]Significantly different from Basal Ovx group;
[c]Significantly different from Sham group;
[d]Significantly different from Ovx group.

TABLE 11

Cortical bone morphometry measured at femoralneck cross-sectional areas after eight weeks of treatment with rhIGF-I alone or rhIGF-I/IGFBP-3 complex.

| Parameter | Sham | Ovx | rhIGF-I (mg/kg) | | rhIGF-I (mg/kg) + equimolar rhIGFBP-3 | | |
|---|---|---|---|---|---|---|---|
| | | | 0.9 | 2.6 | 0.9 | 2.6 | 7.5 |
| Entire organ | | | | | | | |
| Cortical bone area (%) | 83.3 ± 1.4 | 78.9 ± 1.7* | 84.3 ± 1.0@ | 84.9 ± 1.3@ | 84.1 ± 1.5@ | 84.7 ± 2.2@ | 87.3 ± 1.4@ |
| Bone marrow area (%) | 13.9 ± 0.1 | 13.1 ± 0.1* | 8.4 ± 0.1*,@ | 6.4 ± 0.1*,@ | 7.8 ± 0.1*,@ | 7.9 ± 0.1*,@ | 3.3 ± 0.02@,c |
| Average cortical with ($\mu$m) | 472 ± 9 | 447 ± 8 | 465 ± 11 | 471 ± 12 | 453 ± 12 | 466 ± 14 | 497 ± 8*,@,c |
| Periosteal envelope | | | | | | | |
| Mineralized surface (%) | 4.2 ± 0.4 | 7.1 ± 1.3* | 7.9 ± 1.4* | 11.8 ± 1.0*,@ | 8.0 ± 0.9* | 9.7 ± 1.7* | 15.4 ± 1.3*,@,c |
| Mineral appositional rate ($\mu$m/d) | 0.24 ± 0.01 | 0.24 ± 0.01 | 0.38 ± 0.03*,@ | 0.48 ± 0.2*,@ | 0.36 ± 0.01*,@ | 0.35 ± 0.01*,@ | 0.48 ± 0.02*,@,b |
| Bone formation rate ($\mu$m$^2$/$\mu$m/d) | 0.01 ± 0.001 | 0.01 ± 0.003 | 0.02 ± 0.01* | 0.04 ± 0.01*,@ | 0.02 ± 0.003* | 0.02 ± 0.01*,b | 0.05 ± 0.01*,@,c |
| Bone formation rate (%/y) | 7.3 ± 0.8 | 9.6 ± 1.3 | 34.7 ± 5.3*,a | 55.4 ± 4.5*,@ | 37.47 ± 6.1*,@ | 37.0 ± 5.8*,@,b | 59.0 ± 6.2†,@,c |
| Endocortical envelope | | | | | | | |
| Mineralized surface (%) | 6.5 ± 0.6 | 8.8 ± 1.3 | 12.2 ± 1.5* | 11.7 ± 1.6* | 19.7 ± 0.9*,@,a | 17.9 ± 2.3*,@,b | 27.6 ± 2.4*,@,c |
| Mineral appositional rate ($\mu$m/d) | 0.23 ± 0.01 | 0.24 ± 0.01 | 0.49 ± 0.02*,@ | 0.49 ± 0.03*,@ | 0.6 ± 0.01*,@,a | 0.53 ± 0.03*,@ | 0.57 ± 0.02*,@,c |
| Bone formation rate ($\mu$m2/$\mu$m/d) | 0.01 ± 0.001 | 0.01 ± 0.002 | 0.05 ± 0.02*,@ | 0.04 ± 0.01*,@ | 0.07 ± 0.01*,@ | 0.08 ± 0.01*,@,b | 0.1 ± 0.01*,@,c |
| Bone formation rate (%/y) | 3.2 ± 0.3 | 5.8 ± 1.1 | 27.8 ± 4.7*,@ | 27.4 ± 5.4*,@ | 46.7 ± 6.9*,@ | 60.6 ± 11.1*,@,b | 79.9 ± 8.5*,@,c |
| Resorption perimeter (%) | 4.8 ± 0.2 | 7.5 ± 0.6* | 5.2 ± 0.6@ | 3.9 ± 0.4*,@ | 4.8 ± 0.4 | 3.9 ± 0.5@,b | 3.2 ± 0.3*,@,c |

Data are expressed as the mean ± SE;
*$P < 0.05$ Significantly different from Sham group;
@$P < 0.05$ Significantly different from Ovx group;
[a]$P < 0.05$ Significantly different from rhIGF-I (0.9 mg/kg) group;
[b]$P < 0.05$ Significantly different from rhIGF-I (2.6 mg/kg) group;
[c]$P < 0.05$ Significantly different from rhIGF-I/IGFBP-3 (0.9 mg/kg and/or 2.6 mg/kg) group.

TABLE 12

Cancellous bone morphometry measured at distal femoral metaphysis after eight weeks of treatment with rhIGF-I alone or rhIGF-I/IGFBP-3 complex.

| | | | rhIGF-I (mg/kg) | | rhIGF-I (mg/kg) + equimolar rhIGFBP-3 | | |
|---|---|---|---|---|---|---|---|
| Parameter | Sham | Ovx | 0.9 | 2.6 | 0.9 | 2.6 | 7.5 |
| Percent double labeled perimeter (%) | 6.05 ± .64 | 17.41 ± 1.56† | 14.21 ± 0.77† | 17.32 ± 1.33† | 18.02 ± 0.84† | 16.23 ± 1.11† | 26.61 ± 2.26†,* |
| Percent resorption perimeter (%) | 5.89 ± 0.3 | 11.01 ± 1.46† | 9.61 ± 0.67† | 14.61 ± 2.07 | 9.08 ± 1.01† | 10.16 ± 0.56†,b | 14.45 ± 0.97†,* |
| Corrected mineral appositional rate (μm/d) | 0.17 ± 0.03 | 0.47 ± 0.06† | 0.38 ± 0.03† | 0.41 ± 0.03† | 0.44 ± 0.02† | 0.44 ± 0.03† | 0.48 ± 0.04† |
| Mineralized surface (%) | 2.52 ± 0.36 | 8.54 ± 1.5† | 5.35 ± 1.79†,* | 6.35 ± 2.44† | 10.48 ± 3.24†,* | 13.56 ± 3.53† | 19.89 ± 4.09†,* |
| Bone formation rate (μm²/μm/d) | 0.001 ± 0.001 | 0.021 ± 0.006† | 0.014 ± 0.001† | 0.012 ± 0.002† | 0.015 ± 0.002† | 0.014 ± 0.002† | 0.036 ± 0.002†,* |
| Endochondral growth (μm/d) | 3.77 ± 0.21 | 3.81 ± 0.29 | 5.57 ± 0.33†,* | 6.44 ± 0.4†,* | 5.89 ± 1.33†,* | 5.89 ± 0.26†,* | 6.15 ± 0.28†,* |
| Percent trabecular area (%) | 25.02 ± 1.58 | 14.95 ± 0.92† | 19.48 ± 0.78†,* | 14.73 ± 1.33† | 16.15 ± 0.99†,a | 17.86 ± 1.41† | 11.64 ± 0.9†,* |
| Trabecular thickness (μm) | 52.35 ± 2.44 | 58.8 ± 1.29† | 66.42 ± 0.58† | 56.37 ± 1.88 | 55.11 ± 1.59 | 68.2 ± 1.2†,*,b | 50.0 ± 2.12* |
| Trabecular number (No/mm) | 4.78 ± 0.21 | 2.53 ± 0.12† | 2.97 ± 0.1†,* | 2.54 ± 0.17† | 2.85 ± 0.13† | 2.74 ± 0.13† | 2.3 ± 0.15† |
| Trabecular separation (μm) | 229.8 ± 12.7 | 492.69 ± 26.2† | 393.9 ± 16.9†,* | 501.1 ± 39.2† | 429.8 ± 22.4† | 447.3 ± 37.1† | 571.7 ± 43.7† |
| Perimeter/Area ratio (mm/mm²) | 32.43 ± 1.54 | 28.48 ± 0.64† | 25.38 ± 0.37†,* | 29.21 ± 1.0 | 29.7 ± 0.89a | 25.9 ± 0.8†,*,b | 33.23 ± 0.83 |

Data are-expressed as the mean ± SE;
†Significantly different from Sham group, P < 0.05 by analysis of variance followed by Dunnett's test;
*Sign ificantly different from Ovx group, P < 0.05 by analysis of variance followed by Dunnett's test;
aSignificantly different from rhIGF-I (0.9 mg/kg) group, P < 0.05 by analysis of variance followed by Fisher's PLSD method;
bSignificantly different from rhIGF-I (2.6 mg/kg) group, P < 0.05 by analysis of variance followed by Fisher's PLSD method.

TABLE 13

Cancellous bone morphometry measured at distal fernoral epiphysis after eight weeks of treatment with rhIGF-I alone or rhIGF-I/IGFBP-3 complex.

| | | | rhIGF-I (mg/kg) | | rhIGF-I (mg/kg) + equimolar rhIGFBP-3 | | |
|---|---|---|---|---|---|---|---|
| Parameter | Sham | Ovx | 0.9 | 2.6 | 0.9 | 2.6 | 7.5 |
| Percent double labeled perimeter (%) | 6.07 ± 0.49 | 18.72 ± 2.02† | 9.35 ± 0.62†,* | 13.43 ± 1.45†,* | 22.89 ± 1.32†,a | 24.12 ± 2.06†,b | 28.24 ± 1.36†,* |
| Percent resorption perimeter (%) | 5.93 ± 0.48 | 7.18 ± 0.57 | 5.11 ± 0.39* | 5.26 ± 0.54* | 4.73 ± 0.49* | 5.19 ± 0.33* | 7.13 ± 0.52 |
| Corrected mineral appositional rate (μm/d) | 0.17 ± 0.05 | 0.51 ± 0.04† | 0.57 ± 0.01† | 0.39 ± 0.04†,* | 0.55 ± 0.02† | 0.58 ± 0.17†,b | 0.7 ± 0.02†,* |
| Mineralized surface (%) | 1.56 ± 0.09 | 9.65 ± 2.58† | 6.01 ± 2.12†,* | 9.28 ± 3.47† | 12.31 ± 3.2†,*,a | 17.71 ± 4.05†,b | 21.39 ± 3.87†,* |
| Bone formation rate (μm²/μm/d) | 0.001 ± 0.003 | 0.016 ± 0.004† | 0.008 ± 0.001† | 0.008 ± 0.002† | 0.016 ± 0.003† | 0.023 ± 0.005†,b | 0.035 ± 0.003†,* |
| Percent trabecular area (%) | 37.19 ± 1.44 | 31.01 ± 0.74† | 41.28 ± 2.06* | 37.8 ± 1.67* | 36.3 ± 1.54*,a | 34.11 ± 0.69 | 40.11 ± 1.73* |
| Trabecular thickness (μm) | 83.9 ± 2.6 | 82.68 ± 3.0 | 93.42 ± 4.13 | 96.5 ± 2.87†,* | 92.04 ± 2.33†,* | 92.01 ± 0.98†,* | 98.79 ± 4.13†,* |
| Trabecular number (No/mm) | 4.33 ± 0.16 | 3.79 ± 0.16† | 4.45 ± 0.14* | 3.71 ± 0.13† | 4.42 ± 0.2* | 3.89 ± 0.1 | 4.07 ± 0.17 |
| Trabecular separation (μm) | 206.4 ± 11.8 | 265.5 ± 11.6† | 191.9 ± 11.9* | 241.1 ± 10.9† | 207.1 ± 11.9* | 240.0 ± 5.7†,* | 210.9 ± 10.9* |
| Perimeter/Area ratio (mm/mm²) | 20.03 ± 0.61 | 20.43 ± 0.89 | 18.2 ± 0.76 | 16.52 ± 0.97†,* | 19.17 ± 1.15 | 18.45 ± 0.41 | 17.06 ± 0.84†,* |

Data are-expressed as the mean ± SE;
†Significantly different from Sham group, P < 0.05 by analysis of variance followed by Dunnett's test;
*Significantly different from Ovx group, P < 0.05 by analysis of variance followed by Dunnett's test;
aSignificantly different from rhIGF-I (0.9 mg/kg) group, P < 0.05 by analysis of variance followed by Fisher's PLSD method;
bSignificantly different from rhIGF-I (2.6 mg/kg) group, P < 0.05 by analysis of variance followed by Fisher's PLSD method.

TABLE 14

Cancellous bone morphometry measured at lumbarvertebralbodies ($L_4$—$L_5$) after eight weeks of treatment with rhIGF-I alone or rhIGF-I/IGFBP-3 complex.

| Parameter | Sham | Ovx | rhIGF-I (mg/kg) | | rhIGF-I (mg/kg) + equimolar rhIGFBP-3 | | |
|---|---|---|---|---|---|---|---|
| | | | 0.9 | 2.6 | 0.9 | 2.6 | 7.5 |
| Percent double labeled perimeter (%) | 8.17 ± 0.99 | 14.2 ± 1.16† | 11.23 ± 0.68 | 14.31 ± 1.47† | 12.0 ± 0.79† | 14.12 ± 1.3† | 16.06 ± 1.21† |
| Percent resorption perimeter (%) | 6.19 ± 0.48 | 8.88 ± 0.97† | 5.37 ± 0.59* | 10.1 ± 1.26† | 6.46 ± 0.57 | 11.34 ± 0.99† | 8.57 ± 0.71† |
| Corrected mineral appositional rate ($\mu$m/d) | 0.13 ± 0.04 | 0.33 ± 0.04† | 0.4 ± 0.01† | 0.32 ± 0.03† | 0.29 ± 0.03†,a | 0.35 ± 0.02† | 0.35 ± 0.04† |
| Mineralized surface (%) | 2.17 ± 0.84 | 7.38 ± 2.46† | 6.28 ± 1.25† | 7.86 ± 1.68† | 7.21 ± 2.15† | 8.56 ± 2.03† | 11.7 ± 4.37† |
| Bone formation rate ($\mu m^2/\mu$m/d) | 0.001 ± 0.001 | 0.008 ± 0.002† | 0.009 ± 0.001† | 0.007 ± 0.002† | 0.011 ± 0.001† | 0.007 ± 0.002† | 0.013 ± 0.003† |
| Percent trabecular area (%) | 36.53 ± 1.89 | 28.46 ± 1.32† | 30.06 ± 1.32† | 35.04 ± 0.97* | 32.95 ± 1.46* | 34.11 ± 2.99* | 37.65 ± 1.57* |
| Trabecular thickness ($\mu$m) | 57.73 ± 2.56 | 57.26 ± 1.58 | 58.62 ± 0.99 | 65.87 ± 3.01†,* | 63.66 ± 3.34†,* | 64.44 ± 3.5†,* | 66.42 ± 2.51†,* |
| Trabecular number (No/mm) | 6.32 ± 0.09 | 4.96 ± 0.17† | 5.12 ± 0.18† | 5.37 ± 0.13* | 5.2 ± 0.15 | 5.25 ± 0.24 | 5.67 ± 0.09* |
| Trabecular separation ($\mu$m) | 145.1 ± 6.05 | 210.2 ± 11.1† | 198.8 ± 10.4†,* | 174.8 ± 3.15* | 186.2 ± 6.7* | 185.0 ± 15.0* | 158.7 ± 16.0* |
| Perimeter/Area ratio (mm/mm²) | 29.51 ± 0.36 | 29.32 ± 0.84 | 28.51 ± 0.48 | 25.69 ± 1.16†,* | 26.73 ± 1.46 | 26.46 ± 1.52 | 25.39 ± 1.05†,* |

Data are-expressed as the mean ± SE;
†Significantly different from Sham group, P < 0.05 by analysis of variance followed by Dunnett's test;
*Significantly different from Ovx group, P < 0.05 by analysis of variance followed by Dunnett's test;
aSignificantly different from rhIGF-I (0.9 mg/kg) group, P < 0.05 by analysis of variance followed by Fisher's PLSD method;
bSignificantly different from rhIGF-I (2.6 mg/kg) group, P < 0.05 by analysis of variance followed by Fisher's PLSD method.

TABLE 15

Cancellous bone morphometry measured at femoralneck cross-sectional areas after eight weeks of treatment with rhIGF-I alone or rhIGF-I/IGFBP-3 complex.

| Parameter | Sham | Ovx | rhIGF-I (mg/kg) | | rhIGF-I (mg/kg) + equimolar rhIGFBP-3 | | |
|---|---|---|---|---|---|---|---|
| | | | 0.9 | 2.6 | 0.9 | 2.6 | 7.5 |
| Percent resorption perimeter (%) | 4.5 ± 0.2 | 10.1 ± 0.8* | 6.1 ± 0.5@ | 5.2 ± 0.4@ | 6.1 ± 0.6@ | 6.9 ± 0.7*,@ | 6.6 ± 0.7*,@ |
| Corrected mineral appositional rate ($\mu$m/d) | 0.23 ± 0.01 | 0.32 ± 0.01* | 0.52 ± 0.04*,@ | 0.54 ± 0.01*,@ | 0.5 ± 0.04*,@,a | 0.52 ± 0.02*,@,b | 0.64 ± 0.04*,@,c |
| Mineralized surface (%) | 5.8 ± 0.7 | 11.9 ± 1.3* | 12.3 ± 0.9* | 13.8 ± 0.9* | 14.9 ± 1.4* | 15.9 ± 2.6* | 19.1 ± 2.2*,@ |
| Bone formation rate ($\mu^2$m/$\mu$m/d) | 0.001 ± 0.001 | 0.006 ± 0.002 | 0.012 ± 0.002* | 0.014 ± 0.003* | 0.014 ± 0.003* | 0.014 ± 0.002* | 0.015 ± 0.003* |
| Percent trabecular area (%) | 12.8 ± 1.9 | 8.1 ± 0.6* | 7.4 ± 1.1* | 8.6 ± 1.3* | 8.1 ± 1.3* | 7.4 ± 0.7* | 9.4 ± 0.8* |
| Trabecular thickness ($\mu$m) | 83.5 ± 6.2 | 69.5 ± 5.4 | 79.9 ± 2.6 | 75.1 ± 3.8 | 69.3 ± 8.6 | 78.3 ± 2.2 | 88.2 ± 6.1*,@,c |
| Trabecular number (No/mm) | 10.8 ± 1.4 | 5.6 ± 0.5* | 6.9 ± 0.9* | 8.1 ± 1.4 | 7.8 ± 0.6* | 5.3 ± 0.6* | 8.5 ± 0.2@,c |
| Trabecular separation ($\mu$m) | 119.4 ± 12.6 | 263.3 ± 17.1* | 206.8 ± 15.2*,@ | 188.3 ± 24.6*,@ | 183.1 ± 20.3*,@ | 186.1 ± 10.3*,@ | 158.4 ± 7.9@ |
| Perimeter/Area ratio (mm/mm²) | 15.7 ± 1.6 | 23.9 ± 2.5* | 19.6 ± 0.8 | 20.7 ± 1.0 | 20.0 ± 2.2 | 18.3 ± 1.3 | 21.9 ± 2.6 |

Data are-expressed as the mean ± SE;
*P < 0.05 Significantly different from Sham group,
@P < 0.05 Significantly different from Ovx group,
aP < 0.05 Significantly different from rhIGF-I (0.9 mg/kg) group,
bP < 0.05 Significantly different from rhIGF-I (2.6 mg/kg) group;
cP < 0.05 Significantly different from rhIGF-I/IGFBP-3 (0.9 mg/kg and/or 2.6 mg/kg) group.

TABLE 16

Structural analyses of cancellous bone performed on von Kossa stained cross-sections of the femoral neck from rats treated for 8 weeks with rhIGF-I alone or the rhIGF-I/IGFBP-3 complex; A nodal analysis was employed for trabecular, and endocortico-trabecular connectivities and star volume analysis for trabecular separation.

| Parameter | Sham | Ovx | rhIGF-I (mg/kg) | | rhIGF-I (mg/kg) + equimolar rhIGFBP-3 | | |
|---|---|---|---|---|---|---|---|
| | | | 0.9 | 2.6 | 0.9 | 2.6 | 7.5 |
| Nodal analysis | | | | | | | |
| Number of nodes | 12.9 ± 1.7 | 6.1 ± 0.5* | 5.5 ± 0.3* | 5.9 ± 0.3* | 7.0 ± 0.7* | 7.6 ± 0.5* | 6.5 ± 0.3* |
| Number of struts | 16.0 ± 1.3 | 9.9 ± 0.4* | 7.3 ± 0.4*,@ | 8.5 ± 0.6* | 8.3 ± 0.7* | 8.6 ± 0.4* | 9.3 ± 0.6* |
| Type of strut (% of total) | | | | | | | |
| Free-free | 5.8 ± 1.2 | 20.6 ± 1.8* | 5.3 ± 2.6@ | 8.7 ± 2.9@ | 6.8 ± 1.9@ | 7.1 ± 2.8@ | 8.4 ± 2.5@ |
| Node-free | 18.9 ± 1.7 | 39.6 ± 2.2* | 29.8 ± 3.6* | 31.3 ± 2.5* | 21.2 ± 5.4@,a | 22.6 ± 1.8@,b | 24.3 ± 1.2@ |
| Node-node | 75.4 ± 2.0 | 39.7 ± 3.1* | 64.9 ± 4.8*,@ | 61.7 ± 3.1*,@ | 68.6 ± 6.2@ | 70.3 ± 3.5@ | 66.4 ± 2.4@ |
| Endocartico-trabecular connectivity | | | | | | | |
| Total number of endocortico-trabecular connections | 11.6 ± 0.9 | 6.8 ± 0.5* | 6.0 ± 0.5* | 6.4 ± 0.5* | 7.8 ± 0.7* | 6.9 ± 0.6* | 7.6 ± 0.9* |
| Endocortico-endocortical (%) | 95.1 ± 1.2 | 42.3 ± 1.4 | 50.2 ± 2.4* | 53.2 ± 2.3*,@ | 54.3 ± 1.7*,@ | 54.8 ± 1.9*,@ | 55.1 ± 2.3*,@ |
| Endocortico-free ending (%) | 4.9 ± 0.3 | 57.7 ± 1.4 | 49.8 ± 2.1* | 46.8 ± 2.0*,@ | 45.7 ± 1.3*,@ | 45.2 ± 1.2*,@ | 44.9 ± 2.1*,@ |
| Star volume analysis | | | | | | | |
| Marrow volume (mm$^3$) | 0.01 ± 0.001 | 0.03 ± 0.004* | 0.01 ± 0.002@ | 0.013 ± 0.005@ | 0.01 ± 0.02@ | 0.01 ± 0.002@ | 0.006 ± 0.001@ |

Data are expressed as the mean ± SE;
*P < 0.05 Significantly different from Sham group;
@P < 0.05 Significantly different from Ovx group;
[a]P < 0.05 Significantly different from rhIGF-I (0.9 mg/kg) group;
[b]P < 0.05 Significantly different from rhIGF-I (2.6 mg/kg) group;
[c]P < 0.05 Significantly different from rhIGF-I/IGFBP-3 (0.9 mg/kg and/or 2.6 mg/kg) group.

Example 3

Recombinant synthesis of IGF-I

Recombinant rhIGF-I was produced using a gene insert coding for the sequence shown in FIG. 11 (SEQ ID NO:1), as detailed below.

Materials

The bacterial strain used is a derivative of Escherichia coli K-12 strain W3110 which has been lysogenized with DE3. (Studier, F. and Moffat, B. [1986] *J. Mol. Biol.* 189: 113–130). This lysogen carries the gene for T7 RNA polymerase under the control of the lacUV5 promoter.

This host strain was transformed with plasmids pER10088 by selection for tetracycline-resistance.

Description of Plasmids

The three expression vectors used in this work are similar to pJU1002 and pJU1003 (Squires, C. H., et al. [1988] *J. Biol. Chem.* 263: 16297–16302) except that the genes inserted downstream of the translational coupler are ubiquitin-IGF (pER10088). In addition, pER 10088 differs from pJU1003 in that it does not contain the synthetic 16 bp adaptor sequence at the 5' end of the tet gene in that plasmid; however, it does contain DNA insertions at the unique PvuII site in the pBR322-derived backbone: pER10088 contains a linker 5' . . . CCTCGAGG . . . 3' at that location.

Description of Gene Inserts

As produced for studies carried out in support of the present invention, the vector pER10088 contained an open reading frame (ORF) comprising (in order 5' to 3') an ATG triplet (initiation), the 76 codons of yeast ubiquitin, 70 synthetic codons of mature human insulin growth factor I (FIG. 11), and a termination codon. In this case, the ORF is positioned relative to the translational coupler exactly as described by Squires et al. (above) for fibroblast growth factor.

IGF Purification

E. coli cells producing IGF-I were broken open using a Gaulin mill or Microfluidizer in 5 volumes/wt (e.g.,1 1/200 g cell paste) of 50 mM sodium acetate and 1 mM EDTA, pH 5.5 while its temperature was maintained at not higher then 10° C. The lysate was checked for the presence of whole *E. coli* cells using a light microscope. To the lysate was added one-hundredth volume of a 10% (w/v) solution of polyethyleneimine and then centrifuged at 10,000 for 20 minutes to separate supernatant from pellet. The pellet was re-extracted twice more in 2.5 volumes of 20 mM potassium phosphate, 20 mM DTT and 2 M urea pH 5.8 and centrifuged as above. The pellet was used for further purification steps.

IGF was extracted from the pellet with 5 volumes/wt of 20 mM Tris pH 8.0 containing 6 M urea, 40 mM DTT and 1 mM EDTA and filtered through a Sartorius 0.8 μ filter. The filtrate was diluted with the same buffer to a final protein concentration of 3 mg/ml, then diluted with 2 volumes of 20 mM Tris and 1 mM EDTA pH 8.0. This mixture was subjected to a DNA removal step using protamine sulfate and Q-Sepharose, according to standard methods. Ubiquitin protein peptidase was added to the mixture to release IGF-I from the ubiquitin IGF-I fusion protein, and IGF-I was refolded overnight at ambient temperature. A typical refolding reaction was carried out at about 1 mg/ml protein concentration, 1.5 to 2 M urea and pH range 8–9 in presence of Tris buffer at 20 to 50 mM and a ratio of DTT/Cystamine of 1. Refolding performed as above yields about 40% of the correctly refolded IGF-I compared to the initial amount of IGF-I.

The refolded IGF-I solution was clarified, buffer was exchanged using ultrafiltration system and loaded onto a cation exchange column equilibrated in 50 mM sodium acetate buffer, pH 5.5. Following the loading of the IGF-I solution onto the column, the column was washed with the equilibration buffer and purified IGF-I was then eluted from the column by application of 20 column volumes of gradient starting with equilibration buffer and finishing with either 0.25 or 0.5 M sodium chloride. The appropriate fractions of pure IGF-I were pooled.

Pooled fractions from the cation exchange column were acidified to pH 2.5 with 10% trifluoroacetic acid (TFA). The solution was filtered through a 0.2 μm filter and loaded onto a Vydac C-4 column equilibrated in 0.1% TFA in water. The column was developed with a linear gradient of 0 to 40% of acetonitrile in 0.1% TFA. The fractions containing purified IGF were assayed by SDS-PAGE, then pooled and lyophilized.

Example 4

Recombinant Synthesis of IGFBP-3

Recombinant rhIGFBP-3 was produced using as a gene insert coding for the sequence shown in FIG. 12 (SEQ ID NO:___), as detailed below. FIGS. 13–15 show alternative exemplary gene sequences that can be used in the present invention according to methods standard in the art or analogous to the procedures described below. FIG. 13 is a preferred coding sequence used in the experiments herein.

Materials

The bacterial strain used in experiments carried out in support of the present invention is a derivative of Escherichia coli K-12 strain W3110 which was lysogenized with DE3. (Studier, F. and Moffat, B. [1986] *J. Mol. Biol.* 189: 113–130). This lysogen carries the gene for T7 RNA polymerase under the control of the lacUV5 promoter. This host strain was transformed with plasmid pDJ12833 by selection for tetracycline-resistance.

Description of Plasmids

The three expression vectors used in this work are similar to pJU1002 and pJU1003 (Squires, C. H., et al. [1988] *J. Biol. Chem.* 263: 16297–16302, incorporated herein by reference) except that the gene was inserted downstream of the translational coupler IGFBP-3 (pDJ12833). In addition, pDJ12833 differs from pJU1003 in that it does not contain the synthetic 16 bp adaptor sequence at the 5' end of the tet gene in that plasmid; however, it does contain DNA insertions at the unique PvuII site in the pBR322-derived backbone: pDJ12833 contains a 385 bp fragment carrying the par locus of pSC101 (Meacock, P. A., and Cohen, S. N. [1980] *Cell* 20: 529–542).

Description of Gene Insert pDJ12833 contains an ORF comprising an ATG triplet followed by the 264 codons of mature human IGFBP-3 (FIG. 13). The amino terminal 95 codons were synthetic; the remainder were derived from the natural cDNA for this gene.

In this case, the ORF was positioned relative to the translational coupler exactly as described by Squires et al. ([1988] *J. Biol. Chem.* 263:16297–16302, incorporated herein by reference) for fibroblast growth factor.

IGFBP-3 purification

The *E. coli* cells producing IGFBP-3 ("BP-3") were broken open using a Gaulin mill or Microfluidizer in 6 volumes/wt (e.g., 1.2 ½₀₀ g cell paste) of 20 mM Tris-HCl and 5 mM EDTA, pH 8 while its temperature was maintained at not higher then 10° C. The lysate was checked for the presence of whole *E. coli* cells by light microscopy and then centrifuged at 10,000 g for 20 minutes to separate supernatant from pellet. The pellet was re-extracted twice more in 3 volumes of 20 mM Tris-HCl pH 8 and centrifuged as above. The resulting pellet was used for further purification.

BP-3 was extracted from the pellet with 2.5 volumes/wt of 20 mM Tris pH 8.0 containing 6 M GdHCl, 25 mM DTT and 5 mM EDTA and filtered through a Sartorius 0.8 μ filter. The filtrate was diluted with the above buffer to a final protein concentration of 4 mg/ml followed with 1 volume of 20 mM Tris and 5 mM EDTA pH 8.0. This mixture was subjected to a DNA removal step using protamine sulfate, according to standard procedures known in the art. The protamine sulfate precipitate was removed by filtration, and BP-3 was subjected to the refolding reaction. A typical refolding reaction was effected at about 0.5 to 1 mg/ml protein concentration, 1.0 to 1.5 M GdHCl at pH 8–9 in the presence of Tris buffer at 20 to 50 mM, having reducing/oxidizing agents molar ratio of 1. Refolding performed as above results in greater than 60% of the initial amount of BP-3.

The refolded BP-3 solution was clarified, buffer was exchanged using an ultrafiltration system and loaded onto a cation exchange column equilibrated in 20 mM sodium phosphate buffer, pH 7. Following loading of the BP-3 post-refolding solution onto a cation exchange column, the column was washed with the equilibration buffer and purified BP-3 was then eluted from the column by application of 20 column volumes of gradient starting with equilibration buffer and finishing with 0.8 M sodium chloride. The appropriate fractions of BP-3 were pooled.

The salt concentration of the pooled BP-3-containing fractions was increased to 0.6 M with ammonium sulfate, and then loaded onto a hydrophobic interaction chromatography matrix column equilibrated with salt containing acetate/phosphate buffer having a pH between 5 to 6. BP-3 was eluted with a linear ammonium sulfate gradient ending with 0% ammonium sulfate buffered at pH 5–6. The appropriate fractions were then pooled and saved.

The pooled fractions containing BP-3 were brought to 0.1% trifluoroacetic acid (TFA), and the solution was loaded onto a C4 RP-HPLC column equilibrated with 0.1% TFA in water. The column was washed with equilibration buffer and then eluted with a linear gradient of acetonitrile containing 0.1% TFA. The fractions containing BP-3 were pooled and lyophilized.

We claim:

1. A method for stimulating bone formation in a subject who has a connective tissue disorder causing bone loss, said method comprising administering to the subject pharmaceutically effective doses of IGF-I and IGFBP-3.

2. The method of claim 1 wherein the connective tissue disorder is selected from the group consisting of osteogenesis imperfecta, Ehlers-Danlos syndrome, Marfans syndrome, cutis laxa, homocystinuria, Mankes's syndrome and scurvy.

3. The method of claim 2 wherein a pharmaceutically effective dose of an inhibitor of bone resorption is also administered.

4. The method of claim 1 wherein said doses comprise a 1:1 molar ratio of IGF-I to IGFBP-3.

5. The method of claim 1 wherein said connective tissue disorder is osteoarthritis-related bone loss.

6. The method of claim 5 wherein a pharmaceutically effective dose of an inhibitor of bone resorption is also administered.

7. The method of claim 5 wherein doses comprise a 1:1 molar ratio of IGF-I to IGFBP-3.

8. The method of claim 7 wherein said doses comprise from 1 $\mu$g to 10 mg/kg of body weight of said subject.

* * * * *